(12) United States Patent
Mizukusa et al.

(10) Patent No.: US 8,824,878 B2
(45) Date of Patent: Sep. 2, 2014

(54) ILLUMINATION DEVICE AND INSPECTION DEVICE OF TIRE

(75) Inventors: Hirokatsu Mizukusa, Osaka (JP); Hitoshi Nakamoto, Osaka (JP); Wataru Otani, Osaka (JP)

(73) Assignees: Toyo Tire & Rubber Co., Ltd., Osaka-Shi (JP); Nihon Kizai Co., Ltd., Osaka-Shi (JP)

( * ) Notice: Subject to any disclaimer, the term of this patent is extended or adjusted under 35 U.S.C. 154(b) by 28 days.

(21) Appl. No.: 13/156,680

(22) Filed: Jun. 9, 2011

(65) Prior Publication Data
US 2012/0134656 A1    May 31, 2012

(30) Foreign Application Priority Data

Nov. 25, 2010 (JP) ................................. 2010-262749
Nov. 25, 2010 (JP) ................................. 2010-262753
Dec. 6, 2010 (JP) ................................. 2010-271684

(51) Int. Cl.
*A61B 3/12* (2006.01)
*A61B 3/14* (2006.01)
*G06K 9/00* (2006.01)

(52) U.S. Cl.
CPC ... *A61B 3/12* (2013.01); *A61B 3/14* (2013.01); *A61B 3/145* (2013.01); *A61B 38/156* (2013.01); *G06K 9/00604* (2013.01)
USPC .............................. 396/19; 356/237.2; 362/35

(58) Field of Classification Search
CPC ..... G01V 8/02; G03B 37/005; G01B 11/0625
USPC ............... 356/237.2; 362/35; 396/19; 306/19
See application file for complete search history.

(56) References Cited

U.S. PATENT DOCUMENTS

| | | | | |
|---|---|---|---|---|
| 4,910,411 A | * | 3/1990 | Teraguchi et al. | 250/559.44 |
| 6,069,966 A | * | 5/2000 | Jones et al. | 382/100 |
| 6,144,033 A | * | 11/2000 | Kokubu et al. | 250/358.1 |
| 6,433,874 B2 | * | 8/2002 | Lindsay et al. | 356/458 |
| 6,600,567 B2 | * | 7/2003 | Kaneko et al. | 356/601 |
| 6,680,471 B2 | * | 1/2004 | Kokubu et al. | 250/225 |

(Continued)

FOREIGN PATENT DOCUMENTS

| | | | | |
|---|---|---|---|---|
| JP | 2001-249012 | * | 9/2001 | G01B 11/24 |
| JP | 2001-249012 A | | 9/2001 | |

(Continued)

OTHER PUBLICATIONS

Office Action dated Apr. 22, 2014, issued in corresponding Japanese Patent Application No. 2010-262753, with English Translation (10 pages).

*Primary Examiner* — Clayton E LaBalle
*Assistant Examiner* — Kevin Butler
(74) *Attorney, Agent, or Firm* — Westerman, Hattori, Daniels & Adrian, LLP

(57) ABSTRACT

Disclosed are an illumination device and an inspection device of a tire that can easily detect abnormality of the shape of the manufactured tire. A photographing portion 18,19 photographs a inner peripheral surface of a tire T, while a driving portion 12 relatively rotates the tire T and a inspection portion 20 around an axis of the tire T, in the state of irradiating a light from a light source unit 36 disposed along the inner peripheral surface of the tire T toward the circumferential direction of the tire T.

12 Claims, 25 Drawing Sheets

(56) References Cited

U.S. PATENT DOCUMENTS

| | | | |
|---|---|---|---|
| 6,840,097 B1* | 1/2005 | Huber et al. | 73/146 |
| 6,934,018 B2* | 8/2005 | Shaw et al. | 356/237.2 |
| 7,177,740 B1* | 2/2007 | Guangjun et al. | 73/146 |
| 7,187,437 B2* | 3/2007 | Shaw et al. | 356/237.2 |
| 7,400,702 B2* | 7/2008 | Tahara et al. | 378/61 |
| 7,421,108 B2* | 9/2008 | Kaneko et al. | 382/141 |
| 7,466,430 B2* | 12/2008 | Braghiroli | 356/607 |
| 7,997,129 B2* | 8/2011 | Sukegawa et al. | 73/146.5 |
| 8,059,279 B2* | 11/2011 | Iino et al. | 356/601 |
| 8,141,414 B2* | 3/2012 | Braghiroli | 73/146 |
| 2001/0024279 A1* | 9/2001 | Kaneko et al. | 356/601 |
| 2002/0018218 A1* | 2/2002 | Conheady et al. | 356/602 |
| 2005/0052637 A1* | 3/2005 | Shaw et al. | 356/35.5 |
| 2005/0200838 A1* | 9/2005 | Shaw et al. | 356/237.1 |
| 2005/0264796 A1* | 12/2005 | Shaw et al. | 356/237.2 |
| 2007/0084541 A1* | 4/2007 | Moriguchi et al. | 156/117 |
| 2008/0056446 A1* | 3/2008 | Tahara et al. | 378/62 |
| 2008/0147347 A1* | 6/2008 | Shaw et al. | 702/108 |
| 2010/0000310 A1* | 1/2010 | Braghiroli | 73/146 |
| 2010/0326179 A1* | 12/2010 | Moriguchi et al. | 73/146 |
| 2011/0188731 A1* | 8/2011 | Sekiguchi | 382/141 |
| 2011/0288814 A1* | 11/2011 | Mizutani et al. | 702/150 |
| 2012/0082446 A1* | 4/2012 | Kumai | 396/164 |
| 2012/0134656 A1* | 5/2012 | Mizukusa et al. | 396/19 |
| 2013/0128029 A1* | 5/2013 | Leobal et al. | 348/128 |

FOREIGN PATENT DOCUMENTS

| | | | | |
|---|---|---|---|---|
| JP | 2002-286645 | * | 10/2002 | G01N 21/84 |
| JP | 2002-286645 A | | 10/2002 | |
| JP | 2004-205218 A | | 7/2004 | |
| JP | 2005-227055 A | | 8/2005 | |

* cited by examiner

ILLUMINATION DEVICE AND INSPECTION DEVICE OF TIRE

BACKGROUND OF THE INVENTION

1. Field of the Invention

The present invention relates to an illumination device that illuminates an inner peripheral surface of a tire, and an inspection device of a tire.

2. Background Art

Normally, a tubeless tire is vulcanized and becomes a finished tire by stacking members such as an inner liner, a carcass, a belt, and a tread on a molding drum to mold a non-vulcanized tire, charging the same in a mold, performing an extended deformation by shaping using a bladder, and heating the same while pressing against a mold surface. In order to improve mold releasability from the bladder after vulcanizing, a water-soluble releasing agent or the like is applied to an inner liner of an inner surface of the non-vulcanized tire.

In the manufactured tire, linear concave and convex portions extending in a tire width direction may appear on an inner peripheral surface of the tire due to irregularity of members and the like during manufacturing. Specifically, when both end portions of a carcass ply, in which a steel cord or a high strength organic fiber cord is arranged in the tire width direction, are not overlapped with each other but a gap is formed therebetween, a linear concave portion is generated. Furthermore, when the overlap of a joint portion of the carcass ply is greater than a predetermined amount, a linear convex portion is generated. Furthermore, even when the steel cord of the carcass ply is penetrated through the inner liner and is protruded to the inner surface side of the tire, a linear convex portion is generated.

In such a tire, in which linear concave and convex portions exist on the inner peripheral surface, there is a strong concern that the stability of the tire is low. Thus, the existence of concave and convex portions exceeding a predetermined standard value is examined before shipping the tire (for example, see JP-A-2002-286645).

In JP-A-2002-286645, as an illumination device that is used when inspecting the inner peripheral surface of the tire, a device is disclosed which images an inspection region of the inner peripheral surface of the tire illuminated by the lighting of a light emitting portion provided in a light source unit by a CCD, makes a density distribution of light of the inspection region based on the imaged result, calculates a difference between light intensities targeted for each image angle taken by each light source unit in the density distribution, and controls the light emission amount of the light emitting portion.

However, in the illumination device such as JP-A-2002-286645, there is a problem in that, in order to make the light intensity reflected from the inspection region of the inner peripheral surface of the tire uniform, shadows are not cast even when the linear concave and convex portions exist on the inner peripheral surface of the tire, and it is extremely difficult to detect an existence of the concave and convex portions.

Furthermore, when applying the releasing agent to the inner surface of the non-vulcanized tire, the releasing agent floods the joint portion of the inner liner, and a bulge having a height of about 0.2 to 1.0 mm called air stagnation is generated on the inner peripheral surface of the tire.

When the air stagnation exists on the inner peripheral surface of the tire, since there is a fear that an air leakage of the tubeless tire occurs or the durability may decline, the existence of the air stagnation is inspected before shipping the tire (for example, see JP-A-2001-249012 described as below).

JP-A-2001-249012 discloses an inspection device of a tire in which the photographing means photographs light from the inner peripheral surface of the tire reflected by a mirror while relatively rotating a tire and the photographing means around an axis of the tire in the state of illuminating the inner peripheral surface of the tire by the illumination means.

In the inspection device of the tire disclosed in JP-A-2001-249012, the mirror which reflects the light from the inner peripheral surface of the tire to the photographing means is inserted in a recessed portion that is recessed radially outward from a hollow portion of the tire. In such a case, in order to increase a region that can be photographed in a circumferential direction of the tire, since the inner peripheral surface of the tire forms a circular arc shape, the mirror is deeply inserted from the hollow portion into the recessed portion, whereby it is difficult to make the tip portion of the mirror approach the inner peripheral surface of the tire. For that reason, there is a problem in that, in order to increase a region that can be photographed by the photographing means in the circumferential direction of the tire per unit time to reduce the time necessary for the inspection of the whole periphery of the tire, the range of the inner peripheral surface of the tire, which can be imaged by the photographing means, is narrowed, whereby the inner peripheral surface of the tire cannot be inspected over a wide area.

SUMMARY OF THE INVENTION

The present invention was made in view of the above problems, and an object thereof is to provide an illumination device and an inspection device of a tire that can easily detect abnormality of the shape of the manufactured tire.

According to an aspect of the present invention, there is provided an illumination device which illuminates an inner peripheral surface of a tire by light irradiated from a light source unit, wherein the tire and the light source unit are relatively rotated around an axis of the tire in the state of irradiating light from the light source unit, which is disposed along the inner peripheral surface of the tire, toward the circumferential direction of the tire.

Furthermore, according to another aspect of the present invention, there is provided an inspection device of a tire which uses the illumination device in an illumination portion, wherein the inspection device includes an inspection portion that has an illumination portion which illuminates an inner peripheral surface of a tire by light irradiated from a light source unit and a photographing portion which photographs the inner peripheral surface of the tire, and a driving portion that relatively rotates the tire and the inspection portion around the axis of the tire, wherein the photographing portion photographs the inner peripheral surface of the tire, while the driving portion relatively rotates the tire and the inspection portion around the axis of the tire, in the state of irradiating light from the light source unit disposed along the inner peripheral surface of the tire toward the circumferential direction of the tire.

According to still another aspect of the present invention, there is provided an inspection device of a tire which includes an inspection portion which has an illumination portion that illuminates an inner peripheral surface of a tire, a photographing portion that photographs an inner peripheral surface of the tire, and a mirror that is curved along a circumferential direction of the inner peripheral surface of the tire and reflects the light illuminating the inner peripheral surface of the tire to the photographing portion, and a driving portion that relatively rotates the tire and the inspection portion around the axis of the tire, wherein the photographing portion photographs light from the inner peripheral surface of the tire reflected by the mirror disposed along the inner peripheral surface of the tire, while the driving portion relatively rotates the tire and the inspection portion around the axis of the tire, in a state in which the illumination portion illuminates the inner peripheral surface of the tire.

Furthermore, according to still another aspect of the present invention, there is provided an inspection device of a tire which includes a rotation table that rotates a tire around a rotation axis of the tire, and a transport portion that transports the tire, and inspects the tire supported on the rotation table while rotating the tire, wherein the rotation table includes a rotation support portion that supports a side wall portion of the tire, and a rotation driving portion that rotates the rotation support portion around the rotation axis of the tire, the transport portion includes a transport support portion that supports a position which avoids the position supported by the rotation support portion in the side wall portion of the tire, and a vertical driving portion that vertically moves the transport support portion, and the vertical driving portion moves the transport support portion with the tire placed thereon from an upper side of the rotation support portion to a lower side thereof to transfer the tire placed on the transport support portion to the rotation support portion, and moves the transport support portion from the lower side of the rotation support portion with the tire placed thereon to the upper part thereof to transfer the tire placed on the rotation support portion to the transport support portion.

In the present invention, it is possible to easily detect abnormality of the shape of the manufactured tire.

DETAILED DESCRIPTION OF THE INVENTION

Hereinafter, exemplary embodiments of the present invention will be described with reference to the drawings.
(First Embodiment)

Figure 1:
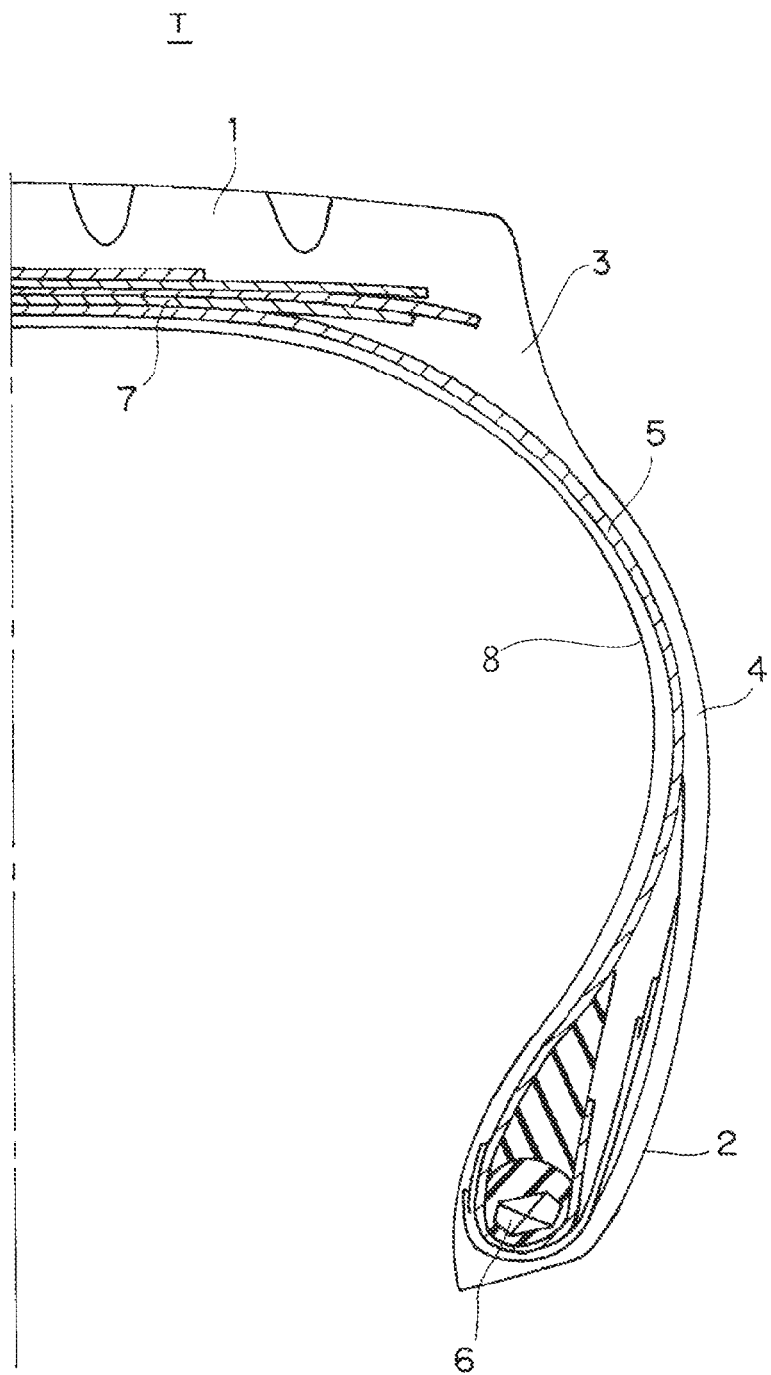
FIG. 1 is a cross-sectional view of a tire that is inspected in an inspection device of a tire according to a first embodiment.

As shown in FIG. 1, a tire T as an inspection target in the present embodiment includes a tread portion 1, a pair of left and right bead portions 2, a pair of left and right shoulder portions 3 interposed between the tread portion 1 and the bead portions 2, and side wall portions 4. A carcass ply 5 is disposed inside the tread portion 1 in a radial direction, the carcass ply 5 being formed of one layer or a plurality of layers in which a steel cord or a high strength organic fiber cord is arranged in a tire radial direction. The carcass ply 5 is locked by being wound up from the inside of the bead core 6 to the outside thereof by the bead portion 2 from the tread portion 1 via both side wall portions 4. Furthermore, in the outside of the carcass ply 5 in the radial direction in the tread portion 1, a plurality of belts 7 formed of a steel cord is disposed.

The tire T having the above configuration is inspected as to whether or not linear concave or convex portions exceeding a predetermined standard value exist on the inner peripheral surface 8 of the tire T by an inspection device of a tire (hereinafter, referred to as an inspection device) 10 shown in FIG. 2 in a final step of the manufacturing process.

The inspection device 10 includes a rotation table 12 on which the tire T is placed with one side wall portion 4 directed downward, a table driving portion 14 that rotates the rotation table 12, an illumination device 16, an inspection portion 20 including photographing portions 18 and 19, an inspection driving portion 22 that moves the inspection 20 in a horizontal direction, and a control portion 24 that drives and controls the table driving portion 14, the illumination device 16, the photographing portions 18 and 19, or the inspection driving portion 22.

Figure 2:
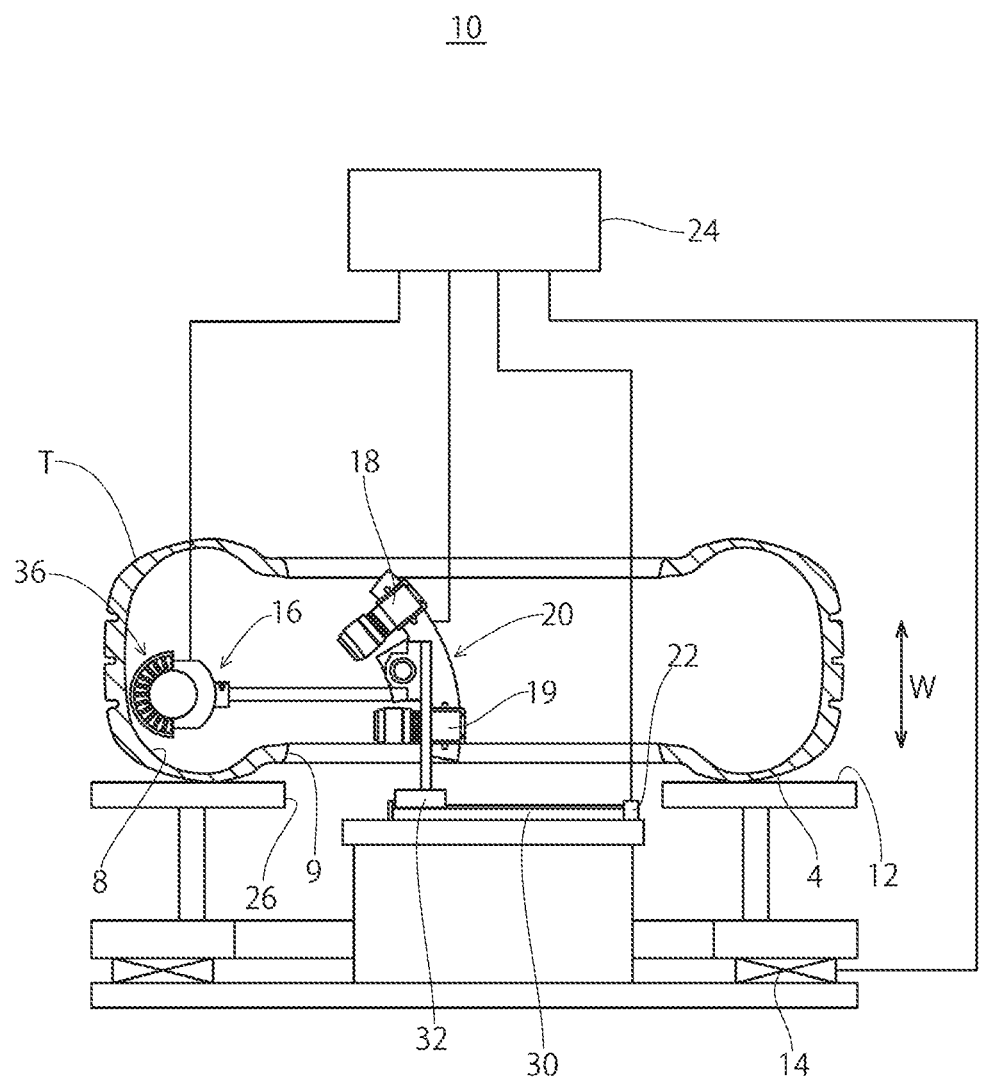
FIG. 2 is a conceptual diagram of the inspection device of the tire according to the first embodiment.
Figure 3:
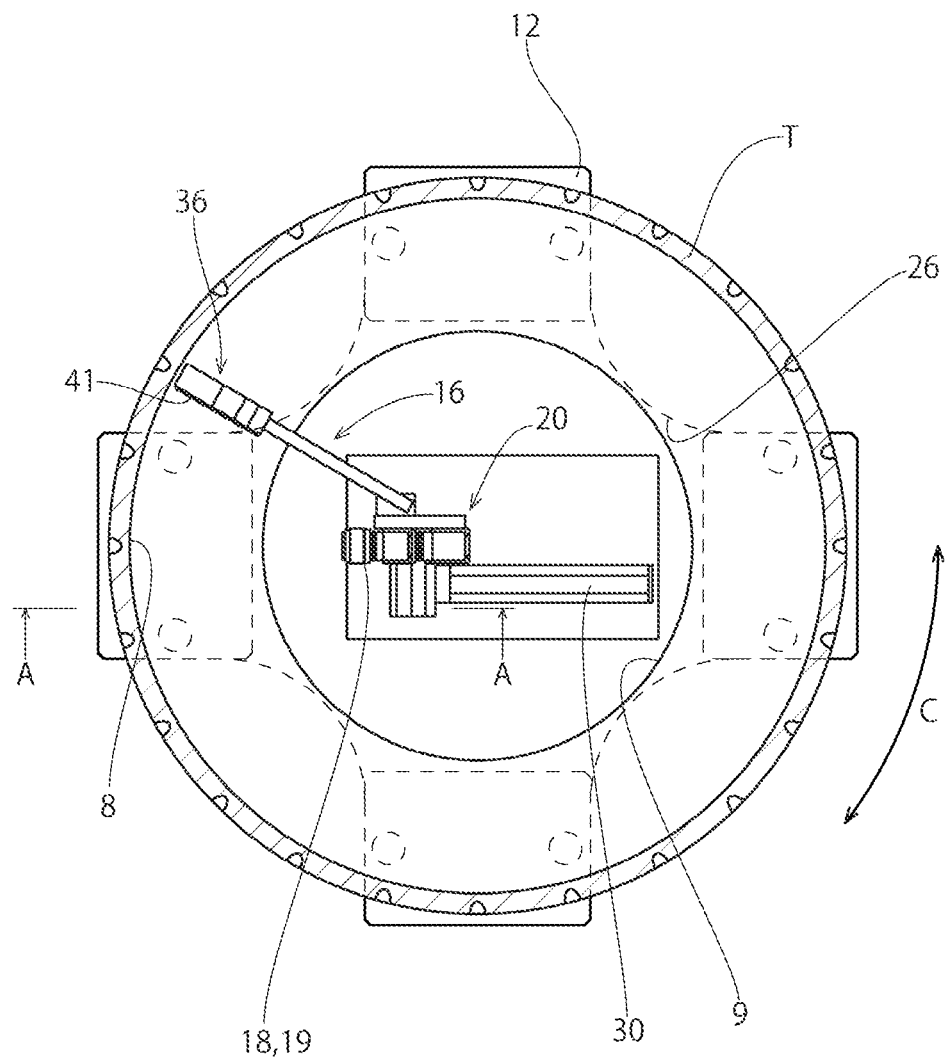
FIG. 3 is a plan view of the inspection device of the tire according to the first embodiment.
Figure 4:
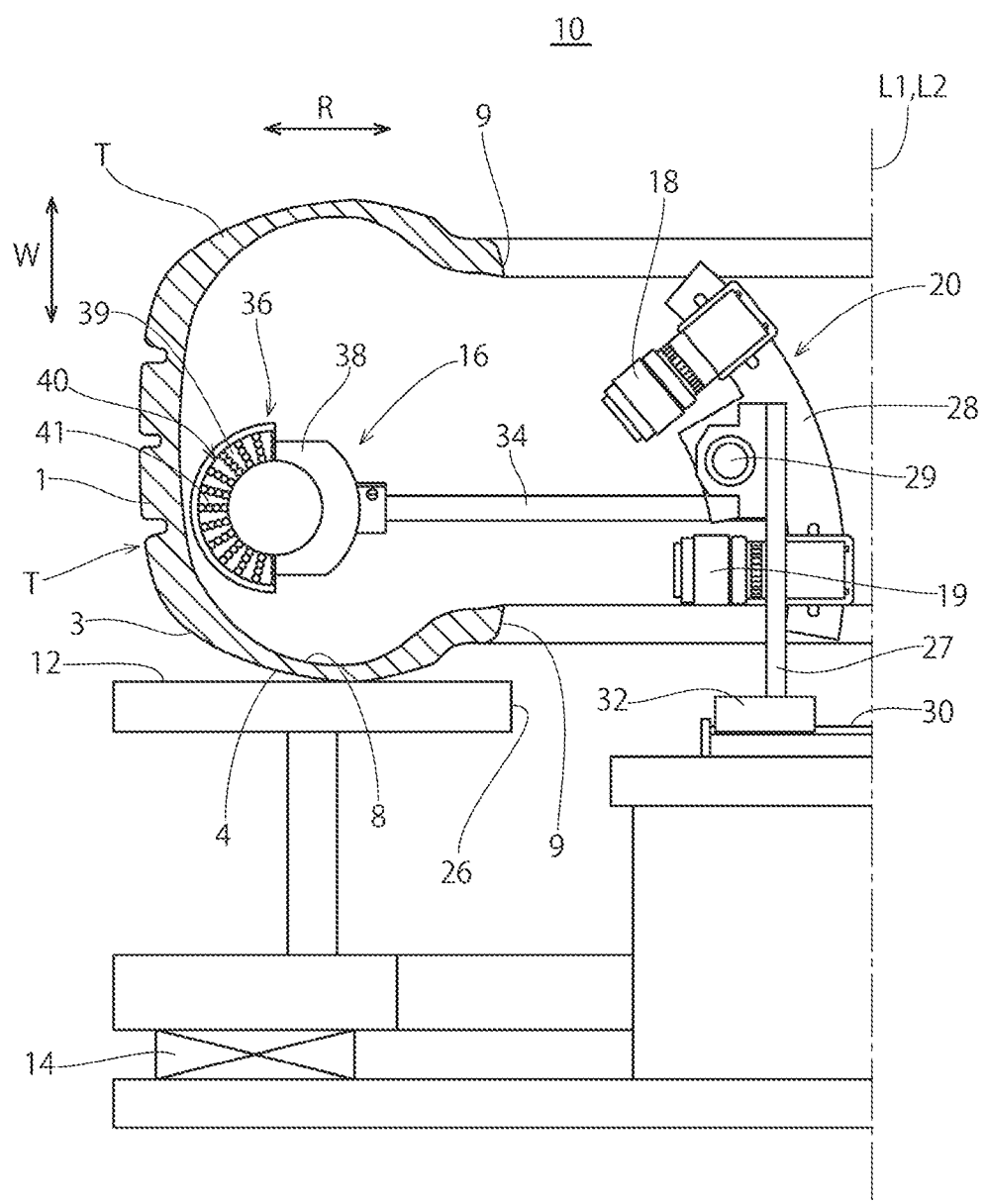
FIG. 4 is a cross-section view taken along a line A-A of FIG. 3.

As shown in FIGS. 2 to 4, the rotation table 12 has a cavity portion 26, and the inspection portion 20 and the inspection driving portion 22 are disposed in the cavity portion 26.

The tire T is placed on the rotation table 12 so that a rotation axis L1 of the rotation table 12 and a rotation axis L2 of the tire T conform to each other. In this manner, a hollow portion 9 formed in the inside of the bead portion 2 of the tire T and a cavity portion 26 of the rotation table 12 are connected above and below in the state in which the tire T is placed on the rotation table 12.

The rotation table 12 rotates the tire T placed thereon around the rotation axis L2 by the transmission of power from the table driving portion 14.

As shown in FIG. 4, the inspection portion 20 is configured such that the illumination device 16, the first photographing portion 18, and the second photographing portion 19 are mounted to a fulcrum 27 protruded upward from the cavity portion 26 of the rotation table 12 via a support frame 28. The inspection portion 20 is inserted from a lower side of the hollow portion 9 of the tire T placed on the rotation table 12. As a result, the illumination device 16, the first photographing portion 18, and the second photographing portion 19 are disposed in the hollow portion 9 of the tire T.

In the inspection portion 20, a lower end portion of the fulcrum 27 is connected to a slider 32 that is provided movably on a rail 30 in a horizontal direction (a left and right direction in FIGS. 2 to 4) by receiving power from the inspection driving portion 22. Furthermore, the upper portion of the fulcrum 27 is connected to the support frame 28 via a pivot shaft 29.

The illumination device 16 includes a support shaft 34 extended from the support frame 28 in the horizontal direction, and a light source unit 36 mounted on a tip portion of the support shaft 34, and irradiates light from the light source unit 36 disposed along the inner surface near the lower end portion of the tread portion 1 to illuminate the inner peripheral surface 8 of the tire T placed on the rotation table 12.

As shown in FIGS. 2 to 4, the light source unit 36 includes a base portion 38 that is provided in a flat plate shape and a ring shape, and a light emitting portion 40 that emits light for illuminating the inner peripheral surface 8 of the tire T.

The base portion 38 is mounted on the tip portion of the support shaft 34 such that one plate surface 39 follows a radial direction R of the tire T and a width direction W of the tire T, that is, the plate surface 39 forms a plane substantially perpendicular to a circumferential direction C of the tire T. The light emitting portion 40 includes a plurality of blue LEDs 41 having a light emission wavelength of 400 to 500 nm, and a plurality of LEDs 41 bulging in a semicircular arc shape toward the inner peripheral surface 8 of the tire T to follow the ring shape of the base portion 38 is arranged and is provided on the plate surface 39 of the base portion 38.

The light source unit 36 of the above configuration irradiates light from the light emitting portion 40 disposed near the inner peripheral surface 8 of the tire T toward the circumferential direction C of the tire T.

The first photographing portion 18 and the second photographing portion 19 are formed of, for example, a CCD camera and photographs the inner peripheral surface 8 of the tire T placed on the rotation table 12.

Specifically, the first photographing portion 18 and the second photographing portion 19 photographs the inner peripheral surface 8 of the tire T, which is situated in front of a progress direction of light emitted from the light emitting portion 40 of the light source unit 36, from a substantially vertical direction when viewed in a plane, that is from the inside of the radial direction R of the tire T toward the outside thereof.

Moreover, the first photographing portion 18 photographs the inner surfaces of the shoulder portion 3, the side wall portion 4, and the bead portion 3 situated in the lower side, and the second photographing portion 19 photographs the inner surface from the shoulder portion 3 situated in the lower side to the center portion of the tread portion 1 in the tire width direction W. That is, in the present embodiment, it is possible to photograph the inner surface from the shoulder portion 3 situated in the lower side to the center portion of the tread portion 1 in the tire width direction W by the first photographing portion 18 and the second photographing portion 19.

The inspection driving portion 22 causes the slider 32 connected to the lower end portion of the fulcrum 27 to slide along the rail 30 in the horizontal direction. As a result, the inspection driving portion 22 moves the inspection portion 20 connected to the fulcrum 27 via the support frame 28 in the horizontal direction. Specifically, the inspection driving portion 22 moves the inspection portion 20 between an evacuation position (see FIG. 5) where the light source unit 36 provided in the illumination device 16 is situated inside the radial direction of the hollow portion 9 of the tire T placed on the rotation table 12, and an inspection position (see FIG. 3) where the light source unit 36 comes close to the inner peripheral surface 8 of the tire T.

The control portion 24 controls the table driving portion 14, the illumination device 16, the photographing portions 18 and 19, or the inspection driving portion 22 based on a program stored in a memory, and performs the inspection of the tire T placed on the rotation table 12.

Figure 5:
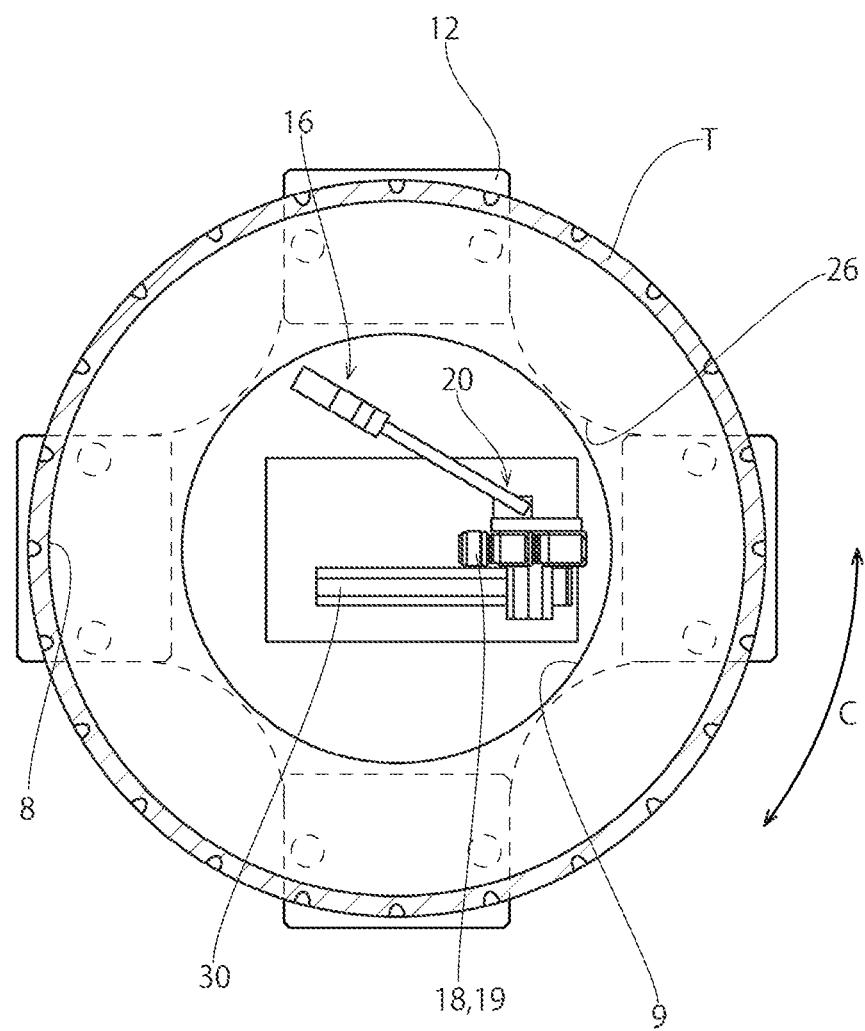
FIG. 5 is a plan view of the inspection device of the tire according to the first embodiment showing the state in which an inspection portion is moved to an evacuation position.

Specifically, firstly, as shown in FIG. 5, the tire T is placed on the rotation table 12 in the state in which the inspection portion 20 is disposed in the evacuation position so that the light source unit 36 does not interfere with the tire T. The tire T placed on the rotation table 12 adjusts the position so that the rotation axis L1 of the rotation table 12 and the rotation axis L2 of the tire T conform to each other by a position adjustment mechanism (not shown).

Next, as shown in FIGS. 2 to 4, the inspection driving portion 22 moves the inspection portion 20 from the evacuation position to the inspection position, makes the light source unit 36 of the illumination device 16 come close to the inner peripheral surface 8 of the tire T, and makes the first photographing portion 18 and the second photographing portion 19 come close to the tire T.

After moving the inspection portion 20 to the inspection position, the inner peripheral surface 8 of the tire T is photographed by the first photographing portion 18 and the second photographing portion 19 in the state in which the control portion 24 causes the LED 41 of the light emitting portion 40 to emit light and irradiates light from the light source unit 36 disposed along the inner peripheral surface 8 of the tire T toward the circumferential direction C of the tire T.

Moreover, the table driving portion 14 rotates the rotation table 12 while maintaining the state of performing the illumination of the inner peripheral surface 8 of the tire T by the illumination device 16 and the photographing of the inner peripheral surface 8 of the tire T by the first photographing portion 18 and the second photographing portion 19, and the tire T and the inspection portion 20 placed thereon are relatively rotated around the rotation axis L2 of the tire T.

As a result, in the state of irradiating light from the light source unit 36 disposed along the inner peripheral surface 8 of the tire T toward the circumferential direction C of the tire T, the first photographing portion 18 and the second photographing portion 19 can consecutively photograph the whole periphery of the inner peripheral surface 8 of the tire T.

The data photographed and obtained from the first photographing portion 18 and the second photographing portion 19 is input to the control portion 24, and the control portion 24 decides whether or not linear concave and convex portions exceeding a predetermined standard value exist by the comparison with predetermined data stored in the memory in advance.

When the photographing is completed all over the whole periphery of the circumferential direction C of the tire T, the inspection of a lower half (that is, from the bead portion 2 situated in the lower side to the center portion of the tread portion 1 in the tire width direction W) of the tire T in the width direction W is completed, and the inspection driving portion 22 moves the inspection portion 20 from the inspection position to the evacuation position.

Moreover, the tire T is turned upside down, the upper half of the width direction W of the tire T, which has not been inspected a moment before, is directed downward and is placed on the rotation table 12, the position of the tire T is adjusted again, the inspection portion 20 is moved from the evacuation position to the inspection position, and in the state of irradiating light from the light source unit 36, the inner peripheral surface 8 of the tire T is photographed by the first photographing portion 18 and the second photographing portion 19 while relatively rotating the tire T around the rotation axis L2.

As mentioned above, in the inspection device 10 of the present embodiment, since the illumination device 16 irradiates light from the light source unit 36 disposed along the inner peripheral surface 8 of the tire T toward the circumferential direction C of the tire T, light can be irradiated to the linear concave and convex portions existing on the inner peripheral surface 8 of the tire T from the transverse direction, and a linear shadow depending on an undulation amount of the concave and convex portions can be generated. For that reason, even when an identification seal of the tire T called a stamp forming, pollution due to a releasing agent, or oil attached during tire manufacturing, or the like exists on the inner peripheral surface 8 of the tire T, it is possible to easily detect whether or not the concave and convex portions exceeding a predetermined standard value exist.

In particular, by making light discharged from the light emitting portion 40 of the illumination device 16 blue, the contrast can be raised without causing halation even in the inner peripheral surface 8 of the black tire T, and the linear shadow generated by the linear concave and convex portions is more easily detected, whereby an inspection accuracy can be improved.

Furthermore, in the inspection device 10 of the present embodiment, the light source unit 36 is formed in a semicircular arc shape in which the light emitting portion 40 bulges toward the inner peripheral surface 8 of the tire T to follow the ring shape of the based portion 38. For that reason, by disposing the light source unit 36 along the inner surface near a boundary portion between the tread portion 1 and the shoulder portion 3, light can be irradiated along the circumferential direction C of the tire T from the position where the light emitting portion 40 comes close not only to the tread portion 1 or the shoulder portion 3 but also to the side wall portion 4, whereby it is possible to easily detect the linear shadow created due to the linear concave and convex portions over the wide range of the inner peripheral surface 8 of the tire T.

In addition, in the aforementioned embodiment, by rotating the tire T relative to the inspection portion 20, the tire T and the inspection portion 20 are relatively rotated, but the inspection portion 20 may be rotated.

Furthermore, in the aforementioned embodiment, after inspecting half of the width direction W of the tire T, the tire T is turned upside down and the remaining half thereof is inspected. However, after the photographing over the whole periphery of the circumferential direction C of the tire T is completed, as shown in FIG. 6, after moving the inspection portion 20 from the lower inspection position to the upper inspection position without moving the inspection portion 20 from the inspection position to the evacuation position, the inner peripheral surface 8 of the tire T may be photographed by the first photographing portion 18 and the second photographing portion 19 while relatively rotating the tire T around the rotation axis L2.

Figure 6:
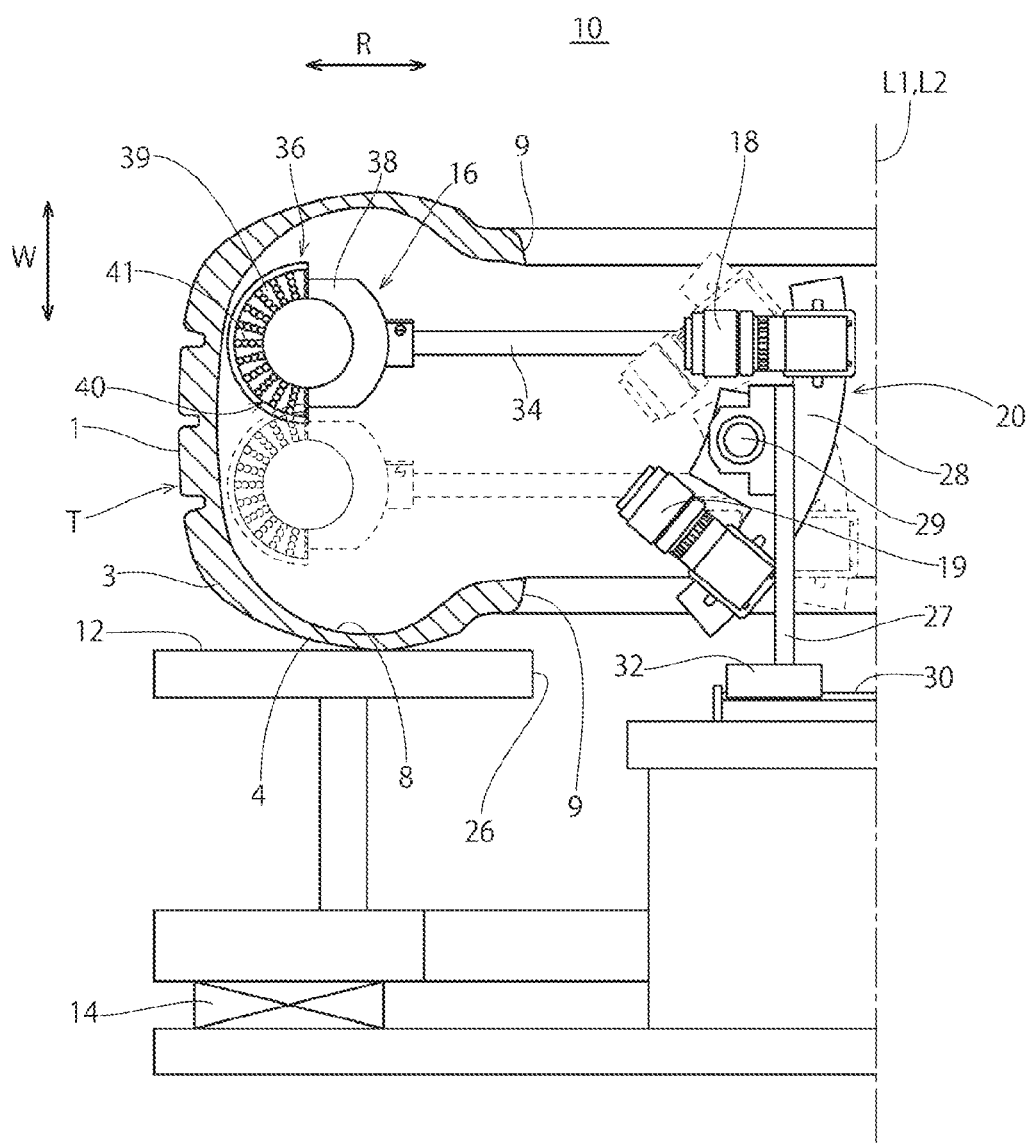
FIG. 6 is an exploded cross-sectional view of major parts of an inspection device of a tire according to a modified example of the first embodiment.

That is, after inspecting half of the width direction W of the tire T, the inspection driving portion 22 moves the illumination device 16 from the lower inspection position shown in FIG. 6 by a dashed-line to the upper side, for example, in the vicinity of the upper end portion of the tread portion 1, and rotates the support frame 28 around the pivot shaft 29 at a predetermined angle, the inner surfaces of the shoulder portion 3, the side wall portion 4, and the bead portion 2 situated in the upper side are photographed by the second photographing portion 19, and the inspection portion 20 is moved to the upper inspection position where the inner surface from the shoulder portion 3 situated in the upper side to the center portion of the tire width direction W of the tread portion 1 is photographed by the first photographing portion 18.

In this case, since the lower side and the upper side of the inner peripheral surface 8 of the tire T can be inspected without being turned upside down, the inspection time can be reduced.

Furthermore, although two photographing portions 18 and are provided in the inspection portion 20 in the aforementioned present embodiment, one or a plurality of photographing portions may be provided without being limited thereto. In particular, by providing a plurality (for example, four) of photographing portions in the inspection portion 20, the whole region of the inner peripheral surface 8 of the tire T can be accurately photographed by one rotation motion of the tire T, whereby the inspection time can be greatly reduced.

(Second Embodiment)

Next, a second embodiment will be described with reference to the drawings.

In the present embodiment, a tire T as an inspection target is the same as the tire T as the inspection target of the aforementioned first embodiment, and the detailed description thereof will be omitted herein.

A tire inspection device of a tire (hereinafter referred to as an inspection device) 110 of the present embodiment inspects whether or not a bulge called an air stagnation exists on the inner peripheral surface 8 of the tire T in the final stage of the manufacturing process.

The inspection device 110 includes a rotation table 112 on which the tire T is placed with one side wall portion 4 directed downward; a table driving portion 114 that rotates the rotation table 112; an inspection portion 120 including a mirror 136, an illumination portion 116, a first photographing portion 118, and a second photographing portion 119; an inspection driving portion 122 that moves the inspection portion 120 in a horizontal direction; and a control portion 124 that drives and controls the table driving portion 114, the illumination portion 116, the photographing portions 118 and 119, or the inspection driving portion 122.

Figure 7:
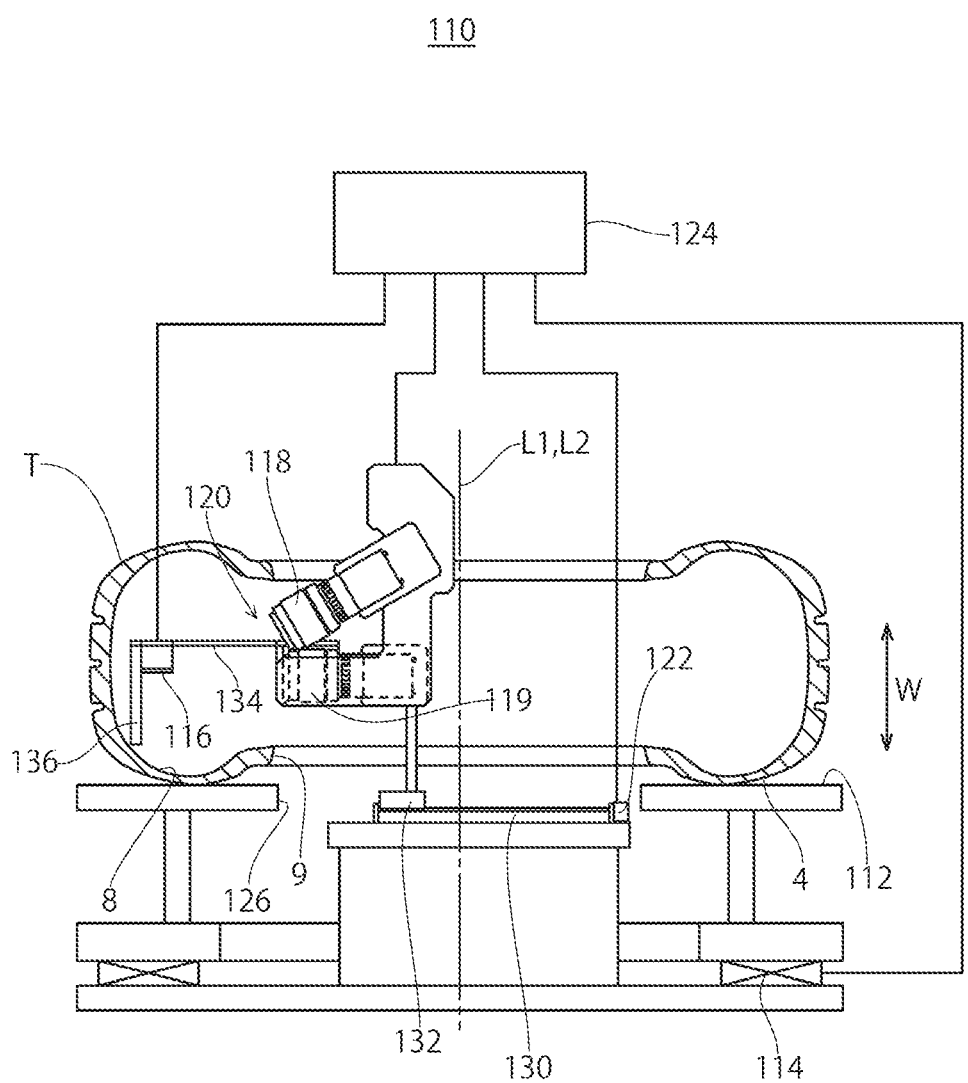
FIG. 7 is a conceptual diagram of a tire according to a second embodiment.
Figure 8:
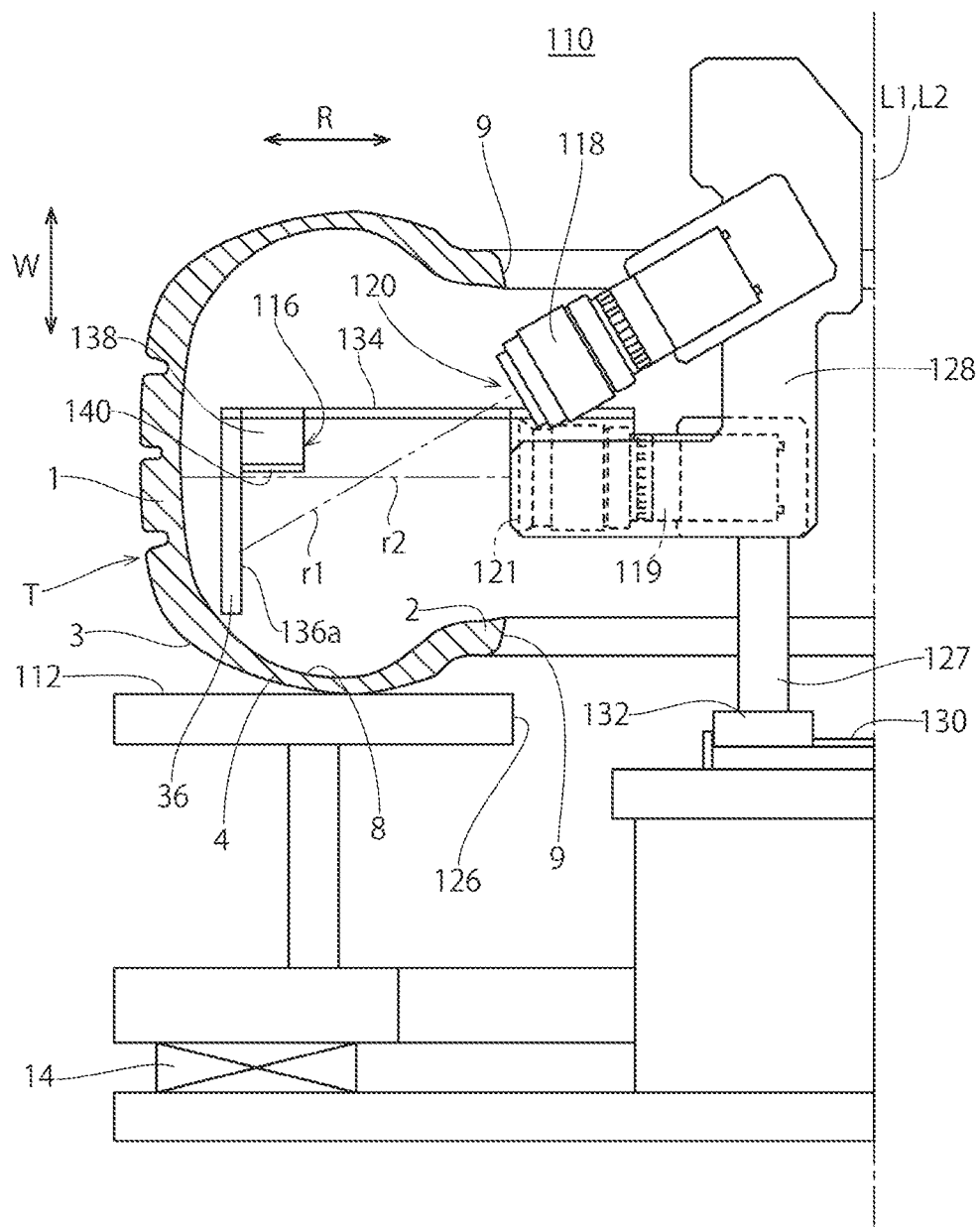
FIG. 8 is an enlarged view of major parts of FIG. 7.

As shown in FIGS. 7 and 8, the rotation table 112 has a cavity portion 126, and the inspection portion 120 and the inspection driving portion 122 are disposed in the cavity portion 126.

The tire T is placed on the rotation table 112 so that a rotation axis L1 of the rotation table 112 and a rotation axis L2 of the tire T conform to each other. In this manner, a hollow portion 9 formed inside the bead portion 2 of the tire T and a cavity portion 126 of the rotation table 112 are connected above and below in the state in which the tire T is placed on the rotation table 112.

The rotation table 112 rotates the tire T placed thereon around the rotation axis L2 by the transmission of power from the table driving portion 114.

Figure 9:
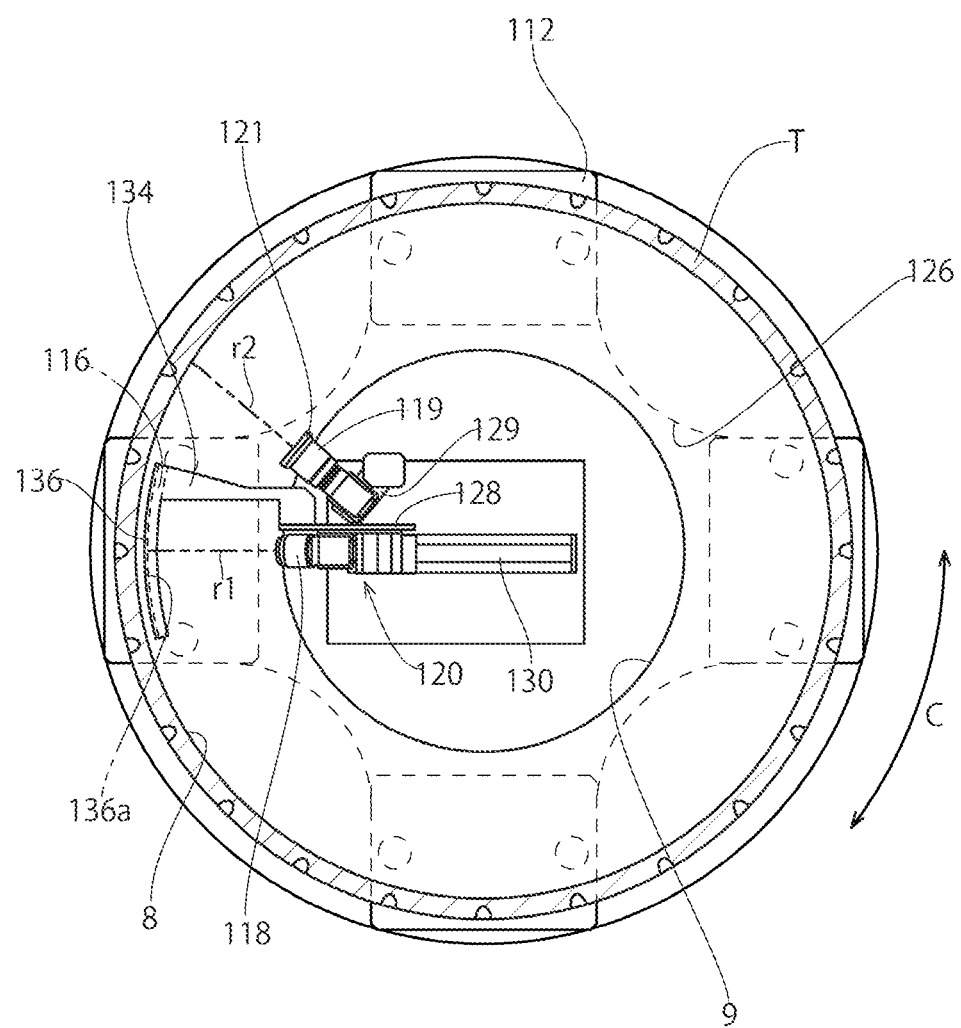
FIG. 9 is a plan view of the inspection device of the tire according to the second embodiment.
Figure 10:
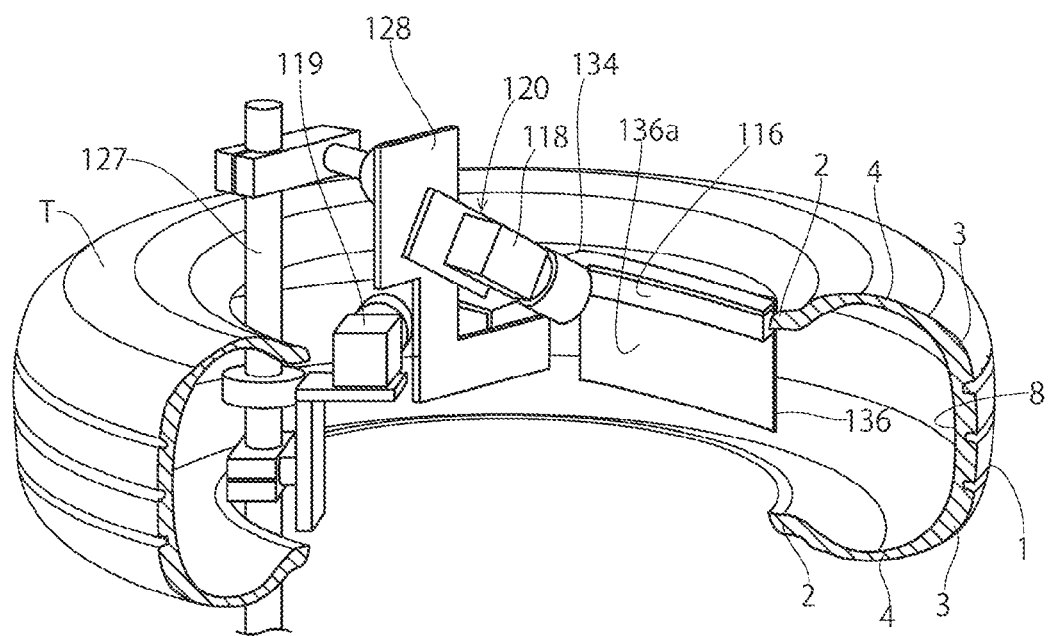
FIG. 10 is a perspective view of the inspection device of the tire according to the second embodiment.

As shown in FIGS. 9 and 10, the inspection portion 120 is mounted to a fulcrum 127, which is protruded upward from the cavity portion 126 of the rotation table 112, via a support frame 128 and a support frame 129. The fulcrum 127 is inserted from a lower side of the hollow portion 9 of the tire T placed on the rotation table 112, whereby the inspection portion 120 is disposed in the hollow portion 9 of the tire T.

A slider 132, which is provided movably on a rail 130 in a horizontal direction (a left and right direction in FIGS. 7 to 9) by receiving power from the inspection driving portion 122, is connected to a lower end portion of the fulcrum 127.

Furthermore, a support frame 128, which fixes the mirror 136, the illumination portion 116, and the first photographing portion 118, is mounted in the upper portion of the fulcrum 127, and a support frame 129, which fixes the second photographing portion 119, is mounted on the lower portion of the support frame 128.

The mirror 136 is mounted on the tip portion of the support material 134 extending from the support frame 128 in the horizontal direction. The mirror 136 is curved along the circumferential direction C of the inner peripheral surface 8 of the tire T. Specifically, in the present embodiment, the mirror 136 is oppositely disposed on the inner surface of the tread portion 1 of the tire T and is curved along the inner surface of the tread portion 1 of the tire T. Since the inner surface (a surface of a side opposite to the surface facing the tread portion 1 of the tire T) of the curved mirror 136 forms a mirror surface 136a, the mirror 136 reflects light illuminating the inner peripheral surface 8 of the tire T to the first photographing portion 118.

The illumination portion 116 includes a base portion 138 that is formed on the upper end portion of the mirror 136 so as to be protruded from the mirror surface 136a, and a light emitting portion 140 that is provided in a lower surface of the base portion 138. The light emitting portion 140 includes a plurality of blue LEDs having a light emission wavelength of 400 to 500 nm, emits light to the lower side, and illuminates from the shoulder portion 3 to the bead portion 2 of the tire T.

The first photographing portion 118 is formed of, for example, a CCD camera, and is fixed to the support frame 128 so that an optical axis r1 slopes downward (see FIG. 8). The first photographing portion 118 reflects the light, which is emitted from the light emitting portion 140 of the illumination portion 116 and illuminates a region from the shoulder portion 3 situated in the lower side of the tire T to the bead portion 2, by the mirror surface 136a of the mirror 136 and takes a photograph. That is, the first photographing portion 118 photographs the inner surfaces of the shoulder portion 3, the side wall portion 4, and the bead portion 2 of the lower side of the tire T projected on the mirror 136.

The second photographing portion 119 is formed of, for example, a CCD camera, and photographs the inner peripheral surface 8 of the tire T placed on the rotation table 112, specifically, the inner surface from the shoulder portion 3 situated in the lower side to the center portion of the tire width direction W of the tread portion 1.

In the second photographing portion 119, in order to avoid the interference between the mirror 136 fixed to the support frame 128, the illumination portion 116, and the first photographing portion 118, an optical axis r2 of the second photographing portion 119 deviates from the optical axis r1 of the first photographing portion 118 when viewed from the plane (see FIGS. 9 and 10).

In addition, in the present embodiment, a ring-shaped illumination portion 121 is mounted around a lens portion of the second photographing portion 119 to illuminate a region photographed by the second photographing portion 119, that is, the inner surface from the shoulder portion 3 situated in the lower side of the tire T placed on the rotation table 112 to the center portion of the tire width direction W of the tread portion 1. The illumination portion 121 emits blue light having a light wavelength of 400 to 500 nm to illuminate the region photographed by the second photographing portion 119.

The inspection driving portion 122 causes the slider 132 connected to the lower end portion of the fulcrum 127 to slide along the rail 130 in the horizontal direction. As a result, the inspection driving portion 122 moves the inspection portion 120 connected to the fulcrum 127 via the support frames 128 and 129 in the horizontal direction. Specifically, the inspection driving portion 122 moves the inspection portion 120 between an evacuation position (see FIG. 11) where the mirror 136 and the illumination portion 116 provided in the tip of the support member 134 are situated inside the radial direction of the hollow portion 9 of the tire T placed on the rotation table 112, and an inspection position (see FIG. 8) where the mirror 136 and the illumination portion 116 come close to the inner peripheral surface 8 of the tire T.

The control portion 124 controls the table driving portion 114, the illumination portion 116, the first photographing portion 118, the second photographing portion 119, the illumination portion 121 or the inspection driving portion 122 based on a program stored in a memory, and performs the inspection of the tire T placed on the rotation table 112.

Figure 11:
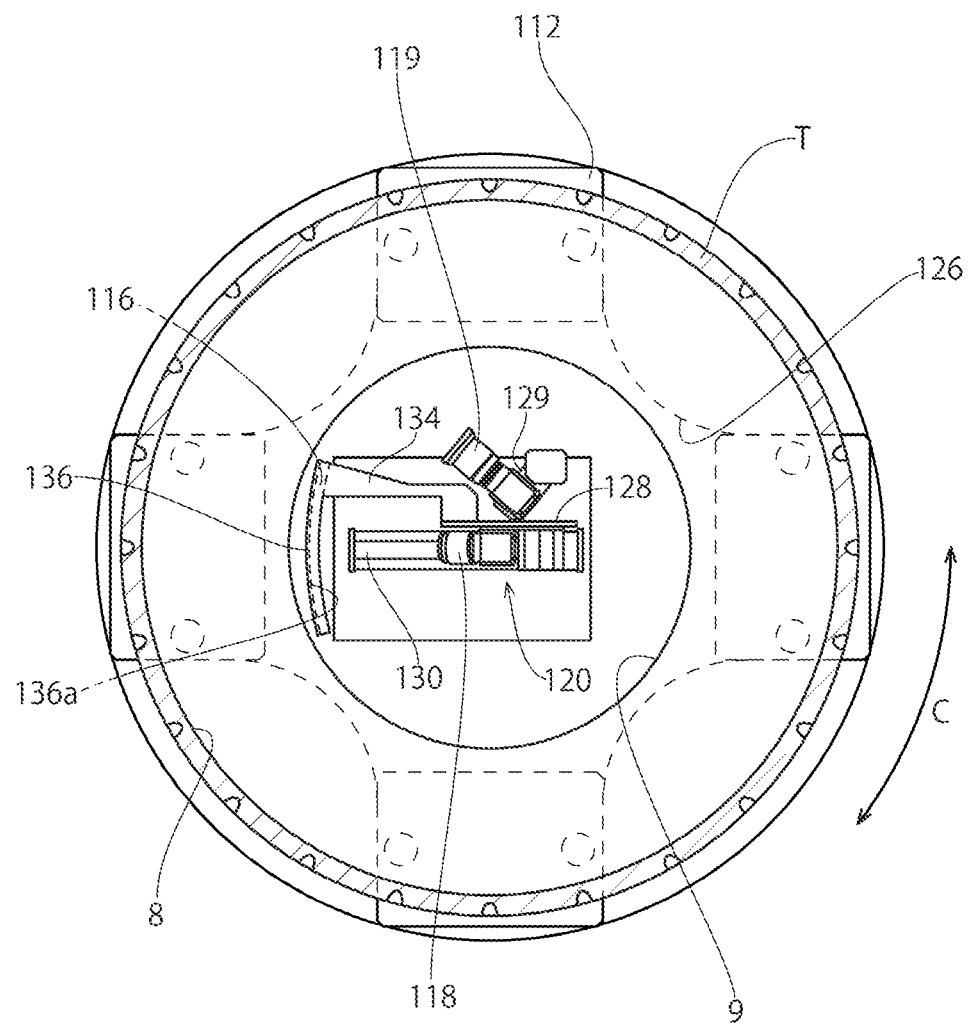
FIG. 11 is a plan view of the inspection device of the tire according to the second embodiment showing the state in which an inspection portion is moved to an evacuation position.

Specifically, firstly, as shown in FIG. 11, the tire T is placed on the rotation table 112 in the state in which the inspection portion 120 is disposed in the evacuation position so that the mirror 136 and the illumination portion 116 provided in the tip of the support material 134 do not interfere with the tire T. The tire T placed on the rotation table 112 adjusts the position so that the rotation axis L1 of the rotation table 112 and the rotation axis L2 of the tire T conform to each other by a position adjustment mechanism (not shown).

Next, the inspection driving portion 122 moves the inspection portion 120 from the evacuation position to the inspection position, makes the mirror 136 and the illumination portion 116 come close to the inner surface of the tread portion 1 of the tire T, and makes the first photographing portion 118 and the second photographing portion 119 come close to the tire T.

After moving the inspection portion 120 to the inspection position, in the state in which the control portion 124 causes the light emitting portion 140 of the illumination portion 116 to emit light and illuminates from the shoulder portion 3 to the bead portion 2 of the tire T, the portion from the shoulder portion 3 to the bead portion 2 of the lower side of the tire T projected on the mirror 136 is photographed by the first photographing portion 118. Furthermore, the control portion 124 photographs the inner surface from the shoulder portion 3 situated in the lower side of the tire T to the center portion of the tire width direction W of the tread portion 1 by the second photographing portion 119, in the state of causing the illumination portion 121 to emit light and illuminating the inner surface from the shoulder portion 3 situated in the lower side of the tire T to the center portion of the width direction W of the tread portion 1 of the tire T, together with the photographing by the first photographing portion 118.

Moreover, as mentioned above, the table driving portion 114 rotates the rotation table 112 while maintaining the state of performing the illumination of the inner peripheral surface 8 of the tire T by the illumination portions 116 and 121 and the photographing of the inner peripheral surface 8 of the tire T by the first photographing portion 118 and the second photographing portion 119, thereby relatively rotating the tire T and the inspection portion 120 placed thereon around the rotation axis L2 of the tire T.

As a result, the first photographing portion 118 and the second photographing portion 119 can consecutively photograph the whole periphery of the inner peripheral surface 8 of the tire T.

The data photographed and obtained from the first photographing portion 118 and the second photographing portion 119 is input to the control portion 124, and the control portion 124 decides whether or not a bulge exceeding a predetermined standard value (for example, a height of about 0.2 to 1.0 nm) exists by the comparison with predetermined data stored in the memory in advance.

When the photographing is completed all over the whole periphery of the circumferential direction C of the tire T, the inspection of a lower half (that is, from the bead portion 2 situated in the lower side to the center portion of the tread portion 1 in the tire width direction W) of the tire T in the width direction W is completed, and the inspection driving portion 122 moves the inspection portion 120 from the inspection position to the evacuation position.

Moreover, the tire T is turned upside down, the upper half of the width direction W of the tire T, which has not been inspected a moment before, is directed downward and is placed on the rotation table 112, the position of the tire T is adjusted again, the inspection portion 120 is moved from the evacuation position to the inspection position, in the state of irradiating light from the illumination portion 116 and the illumination portion 121 to the inner peripheral surface 8 of the tire T, the inner peripheral surface 8 of the tire T is photographed by the first photographing portion 118 and the second photographing portion 119 while relatively rotating the tire T around the rotation axis L2, and the control portion 124 compares predetermined data stored in the memory in advance with the data photographed and obtained to decide whether or not a bulge exceeding the standard value exists.

As mentioned above, in the inspection device 110 of the present embodiment, the mirror 136 reflecting the light, which illuminates the region from the shoulder portion 3 situated in the lower side of the tire T to the bead portion 2, to the first photographing portion 118 is curved along the circumferential direction C of the tread portion 1 of the tire T. Thus, as compared with the case of not curving the mirror, even when a long (large) mirror 136 is provided along the circumferential direction C of the tire T, the mirror 136 can come close to the inner portion of the tread portion 1 of the tire T. For that reason, the region, which can be photographed by the first photographing portion 118 in the circumferential direction C of the tire T per unit time, is increased, and the inner peripheral surface 8 of the tire T can be photographed while reducing the time necessary for inspecting the whole periphery of the tire without creating a blind spot by the first photographing portion 118 and the second photographing portion 119, whereby the whole region of the inner peripheral surface 8 of the tire T can be inspected.

Figure 12:
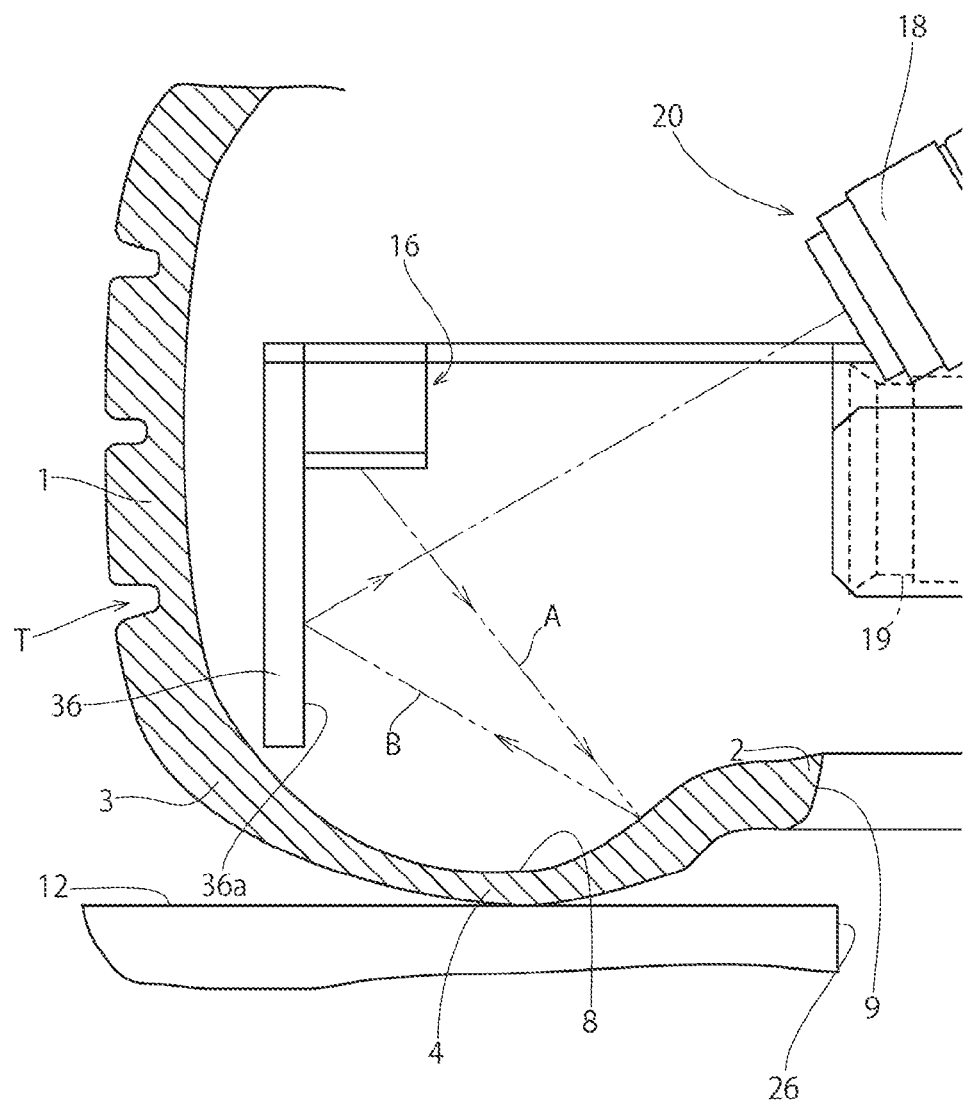
FIG. 12 is an enlarged view of major parts of FIG. 7.

Furthermore, in the inspection device 110 of the present embodiment, the illumination portion 116 is formed on the upper end portion of the mirror 136 so as to be protruded from the mirror surface 136a, irradiates the light toward the inner surface from the shoulder portion 3 to the bead portion 2 of the tire T, and reflects the light, which illuminates the inner surface from the shoulder portion 3 to the bead portion 2 of the tire T, to the first photographing portion 118 by the mirror 136. According to such a configuration, as shown in FIG. 12, it is possible to suitably shift a progress direction A of light emitted from the illumination portion 116 and a photographing direction B by which the first photographing portion 118 photographs the inner peripheral surface 8 of the tire T via the mirror 136. Thus, it is possible to photograph the bulge having a height of about 0.2 to 1.0 nm existing in the inner surface from the shoulder portion 3 to the bead portion 2 of the tire T at a good contrast, which can improve the inspection accuracy.

Furthermore, in the inspection device 110 of the present embodiment, by making light discharged from the light emitting portion 140 of the illumination portion 116 blue, the contrast can be raised without causing halation even in the inner peripheral surface 8 of the black tire T. Thus, even when an identification seal of the tire T called a stamp forming, pollution due to a releasing agent, or oil attached during tire manufacturing, or the like exists on the inner peripheral surface 8 of the tire T, it is easy to detect whether or not the bulge exceeding a standard value exists, whereby an inspection accuracy can be improved.

In addition, in the aforementioned present embodiment, by rotating the tire T relative to the inspection portion 120, the tire T and the inspection portion 120 are relatively rotated, but the inspection portion 120 may be rotated.

Figure 13:
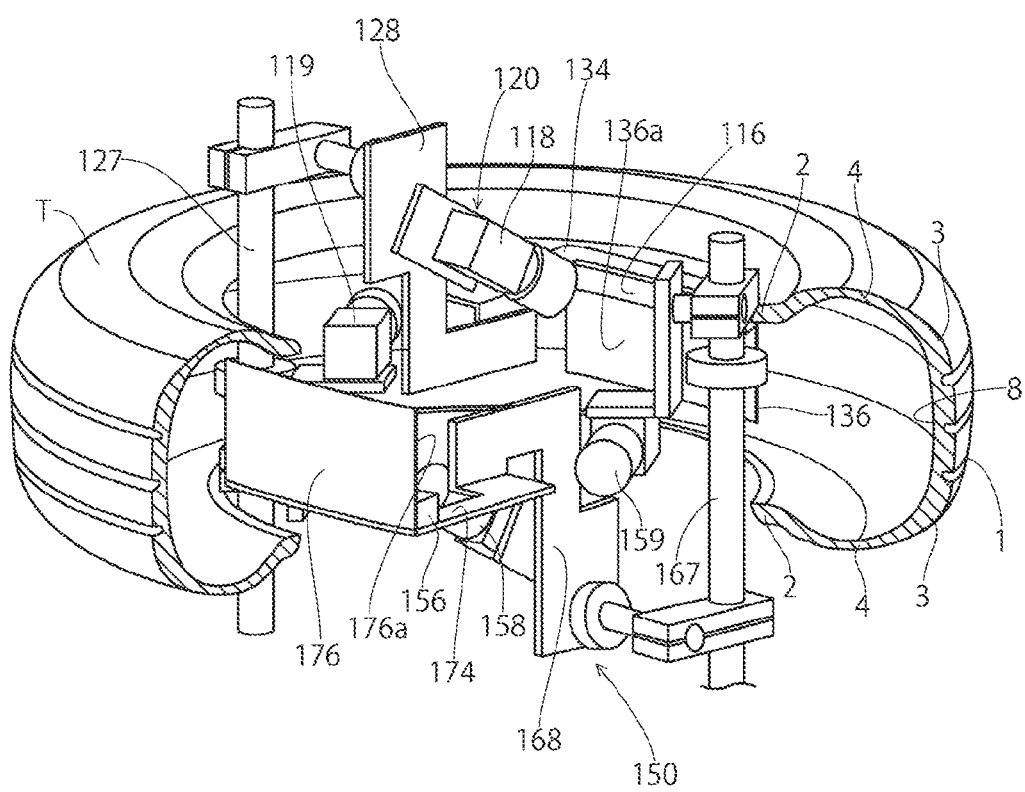
FIG. 13 is a perspective view of an inspection device of a tire according to a modified example of the second embodiment.

Furthermore, although in the aforementioned present embodiment, a case is described where the inspection portion 120 is provided which inspects from the bead portion 2 situated in the lower side of the tire T placed on the rotation table 112 to the center portion of the tire width direction W of the tread portion 1, for example, as shown in FIG. 13, in addition to the inspection portion 120, an upper inspection portion 150, which inspects from the bead portion 2 situated in the upper side of the tire T placed on the rotation table 112 to the center portion of the tire width direction W of the tread portion 1, may be provided in the hollow portion 9 of the tire T to concurrently inspect the lower side and the upper side of the tire T by one rotation motion of the tire T.

That is, the upper inspection portion 150 includes an upper mirror 176, an upper illumination portion 156, a first upper photographing portion 158, and a second upper photographing portion 159. The upper inspection portion 150 is mounted on a fulcrum 167 protruded upward from the cavity portion 126 of the rotation table 112 via a support frame 168 and a support frame 169. In the upper inspection portion 150, the fulcrum 167 is inserted into the hollow portion 9 of the tire T placed on the rotation table 112 from the lower side, and the upper inspection portion 150 is disposed in the hollow portion 9 of the tire T so as to avoid interference with the inspection portion 120.

The support frame 169 with the upper second photographing portion 159 fixed thereto is mounted on the upper portion of the fulcrum 167, and the support frame 168 with the upper mirror 176, the upper illumination portion 156, and the upper first photographing portion 158 fixed thereto is mounted on the lower portion of the support frame 169.

The upper mirror 176 is mounted on the tip portion of a support material 174 that is extended from the support frame 168 in the horizontal direction. The upper mirror 176 is oppositely disposed on the inner surface of the tread portion 1 of the tire T and is curved along the inner surface of the tread portion 1 of the tire T. The upper mirror 176 is disposed in the upper side from the mirror 136 provided in the inspection portion 120. The inside surface (a surface of a side opposite to the surface facing the tread portion 1 of the tire T) of the curved upper mirror 176 forms a mirror surface 176a, whereby the upper mirror 176 reflects light, which illuminates the inner surface from the bead portion 2 of the upper side of the tire T to the shoulder portion 3, to the upper first photographing portion 158.

The upper illumination portion 156 is formed on the upper end portion of the upper mirror 176 so as to be protruded from the mirror surface 176a and emits the light toward the upper side, thereby illuminating from the shoulder portion 3 of the upper side of the tire T to the bead portion 2. The light source of the upper illumination portion 156 is constituted by a blue LED having a light emission wavelength of 400 to 500 nm.

The upper first photographing portion 158 is formed of, for example, a CCD camera, and photographs the inner surfaces of the shoulder portion 3, the side wall portion 4, and the bead portion 2 of the upper side of the tire T projected on the mirror 136.

The upper second photographing portion 159 is formed of, for example, a CCD camera, and photographs the inner surface from the shoulder portion 3 situated in the upper side of the tire T to the center portion of the tire width direction W of the tread portion 1.

In the upper second photographing portion 159, an optical axis of the upper second photographing portion 159 deviates from the optical axis of the upper first photographing portion 158 when viewed from the plane so as to avoid the interference with the upper mirror 176, the upper illumination portion 156, and the upper first photographing portion 118 fixed to the support frame 168.

When an inspection device includes the upper inspection portion 150 in addition to the inspection portion 120, since the lower side and the upper side of the inner peripheral surface 8 of the tire T can be inspected without turning upside down, the inspection time can be reduced.

(Third Embodiment)

Next, a third embodiment will be described with reference to the drawings.

The tire T as an inspection target in the present embodiment is the same as the tire T as the inspection target of the first embodiment, and the detailed description thereof will be omitted herein.

Figure 14:
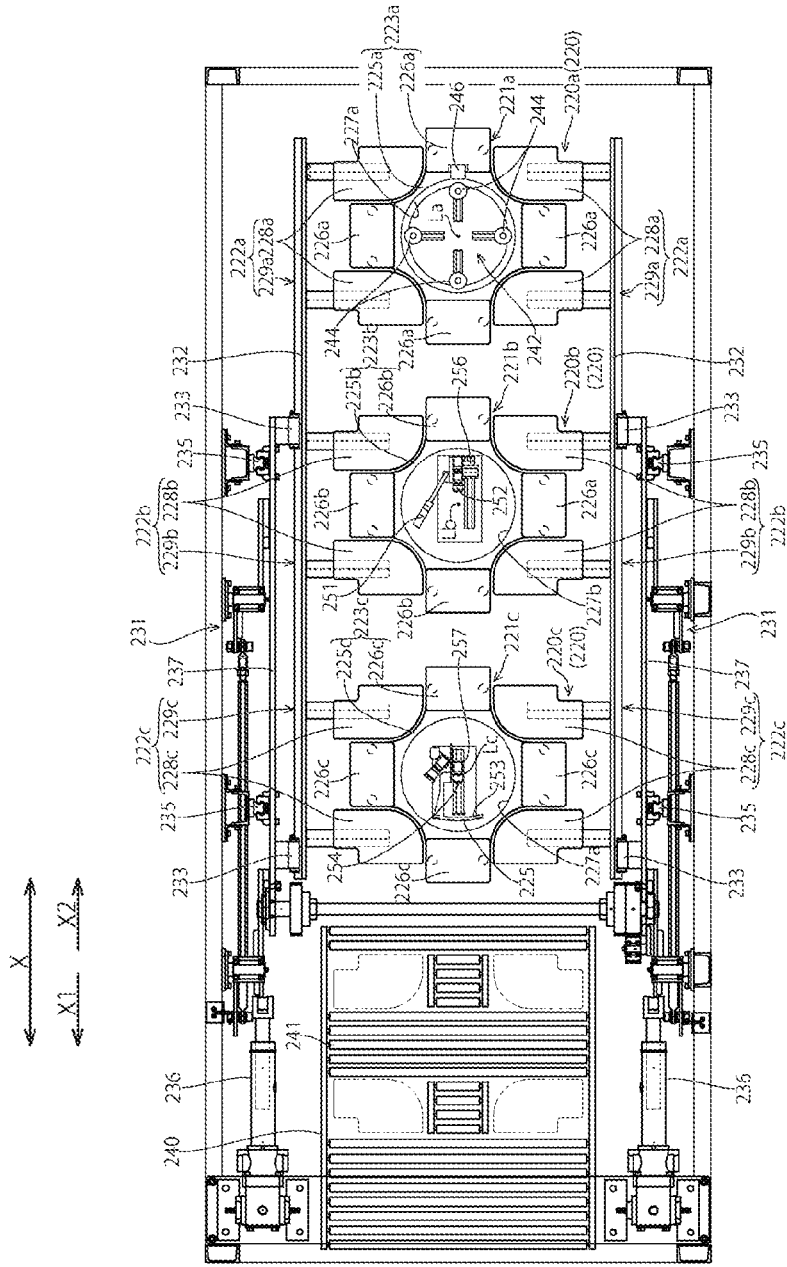
FIG. 14 is a plan view of an inspection device of a tire according to a third embodiment.
Figure 15:
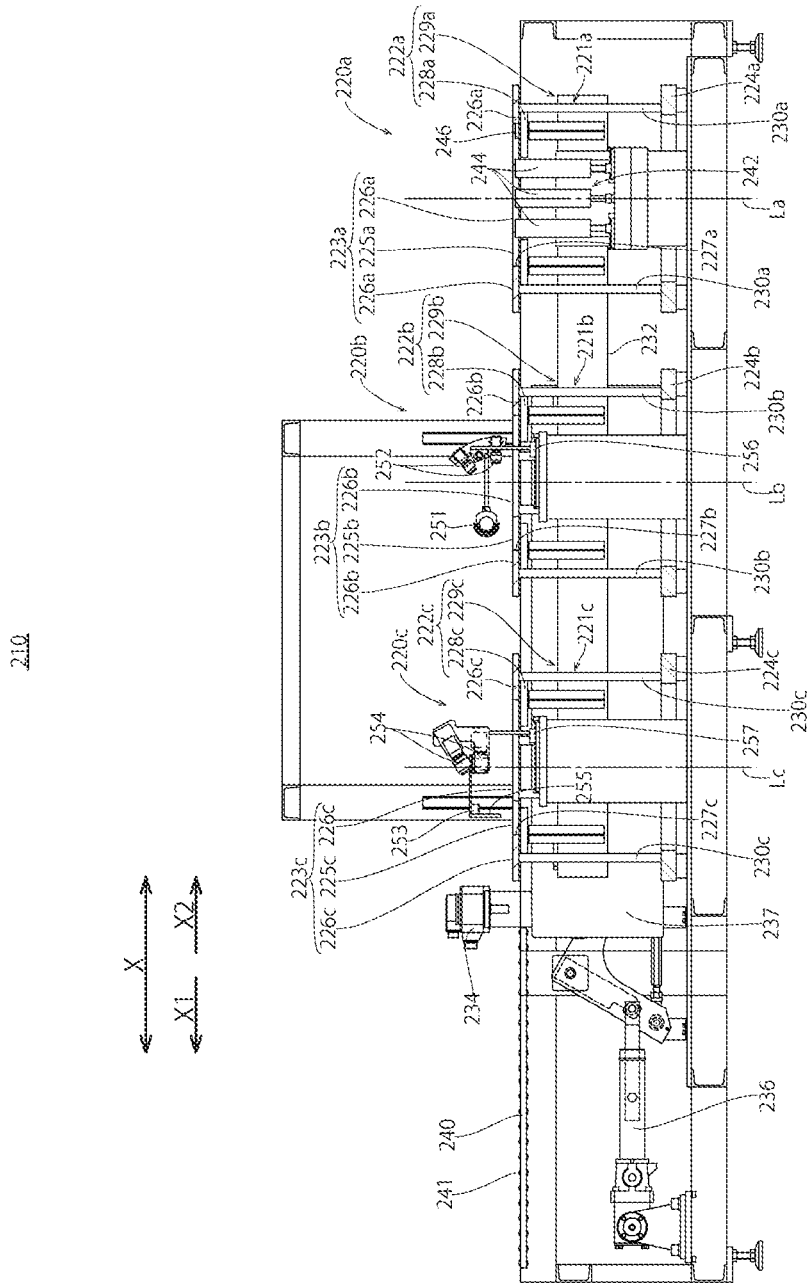
FIG. 15 is a cross-sectional view of the inspection device of the tire according to the third embodiment.

An inspection device 210 of a tire (hereinafter referred to as an inspection device) in the present embodiment inspects the tire T while rotating the tire T, and as shown in FIGS. 14 and 15, a plurality (for example, three in the present embodiment) of inspection portions 220 and carry-out tables 240 is provided in a row at equal intervals.

Among the plurality of provided inspection portions 220, the tire T of the inspection target is placed on a first inspection portion 220a from the outside of the inspection device 210, the tire T transported from the first inspection portion 220a is placed on a second inspection portion 220b disposed adjacently to the first inspection portion 220a, and the tire T transported from the second inspection portion 220b is placed on a third inspection portion 220c.

The first inspection portion 220a includes a rotation table 221a that rotates the tire T around the rotation axis La, and a transport portion 222a that transports the tire T placed on the rotation table 221a to the second inspection portion 220b.

The rotation table 221a includes a rotation support portion 223a that supports the side wall portion 4 of the tire T, and a rotation driving portion 224a that rotates the rotation support portion 223a around the rotation axis La.

The rotation support portion 223a includes a ring-shaped base portion 225a formed with a cavity portion 227a, and a plurality (for example, four in the present embodiment) of support pieces 226a that is disposed on the outer peripheral portion of the base portion 225a in the circumferential direction at intervals. The tire T is placed on the rotation support portion 223a so that the support piece 226a supports the side wall portion 4 of the tire T. In this manner, in the state in which the tire T is placed on the rotation support portion 223a, the hollow portion 9 formed inside the bead portion 2 of the tire T and the cavity portion 227a of the base portion 225a are connected to each other above and below.

The rotation support portion 223a is connected to the rotation driving portion 224a via a fulcrum 230a extended downward from the lower surface of the support piece 226a and is rotated around the rotation axis La by a force that is generated by the rotation driving portion 224a. As a result, the rotation table 221a rotates the tire T placed on the rotation support portion 223a around the rotation axis La.

The transport portion 222a includes a plurality (for example, four in the present embodiment) of transport support portions 228a that supports the lower surface of the side wall portion 4 of the tire T in the circumferential direction of the tire T at intervals, and a vertical driving portion 229a that moves the transport support portions 228a above and below. The plurality of transport support portions 228a is disposed so as to support a position that avoids the position supported by the support piece 226a of the rotation support portion 223a in the side wall portion 4 of the tire T.

The second inspection portion 220b and the third inspection portion 220c only differ in contents to be inspected, and the structures of each inspection portion are identical to each other.

That is, the second inspection portion 220b includes a rotation table 221b, and a transport portion 222b that transports the tire T placed on the rotation table 221b to the third inspection portion 220c.

The rotation table 221b includes a rotation support portion 223b that supports the side wall portion 4 of the tire T, and a rotation driving portion 224b that rotates the rotation support portion 223b around the rotation axis Lb.

The rotation support portion 223b includes a ring-shaped base portion 225b formed with a cavity portion 227b, and a plurality (for example, four in the present embodiment) of support pieces 226b that is disposed on the outer peripheral portion of the base portion 225b in the circumferential direction at intervals. The tire T is placed on the rotation support portion 223b so that the support piece 226b supports the side wall portion 4 of the tire T. In this manner, in the state in which the tire T is placed on the rotation support portion 223b, the hollow portion 9 formed inside the bead portion 2 of the tire T and the cavity portion 227b of the base portion 225b are connected to each other above and below.

The rotation support portion 223b is connected to the rotation driving portion 224b via a fulcrum 230b extended downward from the lower surface of the support piece 226b and is rotated around the rotation axis Lb by a force that is generated by the rotation driving portion 224b. As a result, the rotation table 221b rotates the tire T placed on the rotation support portion 223b around the rotation axis Lb.

The transport portion 222b includes a plurality (four in the present embodiment) of transport support portions 228b that supports the lower surface of the side wall portion 4 of the tire T in the circumferential direction of the tire T at intervals, and a vertical driving portion 229b that moves the transport support portions 228b above and below. The plurality of transport support portions 228b is disposed so as to support a position that avoids the position supported by the support piece 226b of the rotation support portion 223b in the side wall portion 4 of the tire T.

Furthermore, the third inspection portion 220*c* includes a rotation table 221*c*, and a transport portion 222*c* that transports the tire T placed on the rotation table 221*c* to a carry-out portion 240 that is provided adjacently to the third inspection portion 220*c*.

The rotation table 221*c* includes a rotation support portion 223*c* that supports the side wall portion 4 of the tire T, and a rotation driving portion 224*c* that rotates the rotation support potion 223*c* around the rotation axis Lc.

The rotation support portion 223*c* includes a ring-shaped base portion 225*c* formed with a cavity portion 227*c*, and a plurality (for example, four in the present embodiment) of support pieces 226*c* that is disposed on the outer peripheral portion of the base portion 225*c* in the circumferential direction at intervals. The tire T is placed on the rotation support portion 223*c* so that the support piece 226*c* supports the side wall portion 4 of the tire T. In this manner, in the state in which the tire T is placed on the rotation support portion 223*c*, the hollow portion 9 formed inside the bead portion 2 of the tire T and the cavity portion 227*c* of the base portion 225*c* are connected to each other above and below.

The rotation support portion 223*c* is connected to the rotation driving portion 224*c* via a fulcrum 230*c* extended downward from the lower surface of the support piece 226*c* and is rotated around the rotation axis Lc by a force that is generated by the rotation driving portion 224*c*. As a result, the rotation table 221*c* rotates the tire T placed on the rotation support portion 223*c* around the rotation axis Lc.

The transport portion 222*c* includes a plurality (four in the present embodiment) of transport support portions 228*c* that supports the lower surface of the side wall portion 4 of the tire T in the circumferential direction of the tire T at intervals, and a vertical driving portion 229*c* that moves the transport support portions 228*c* above and below. The plurality of transport support portions 228*c* is disposed so as to support a position that avoids the position supported by the support piece 226*c* of the rotation support portion 223*c* in the side wall portion 4 of the tire T.

In the present embodiment, the vertical driving portion 229*a* provided in the first inspection portion 220*a*, the vertical driving portion 229*b* provided in the second inspection portion 220*b*, and the vertical driving portion 229*c* provided in the third inspection portion 220*c* are constituted by a common transport mechanism 231.

Specifically, the transport support portion 228*a* provided in the first inspection portion 220*a*, the transport support portion 228*b* provided in the second inspection portion 220*b*, and the transport support portion 228*c* provided in the third inspection portion 220*c* are mounted on a connection body 232, and the connection body 232 is mounted on the transport mechanism 231.

The transport mechanism 231 includes a first linear guide 233 that guides the connection body 232 in an arrangement direction X of the inspection portion, a first motor 234 that moves the connection body 232 along the first linear guide 233, a second linear guide 235 that guides a base plate 237 with the first linear guide 233 mounted thereon in an above and below direction, and a driving portion 236 that moves the base plate 237 along the second linear guide 235.

Figure 19:
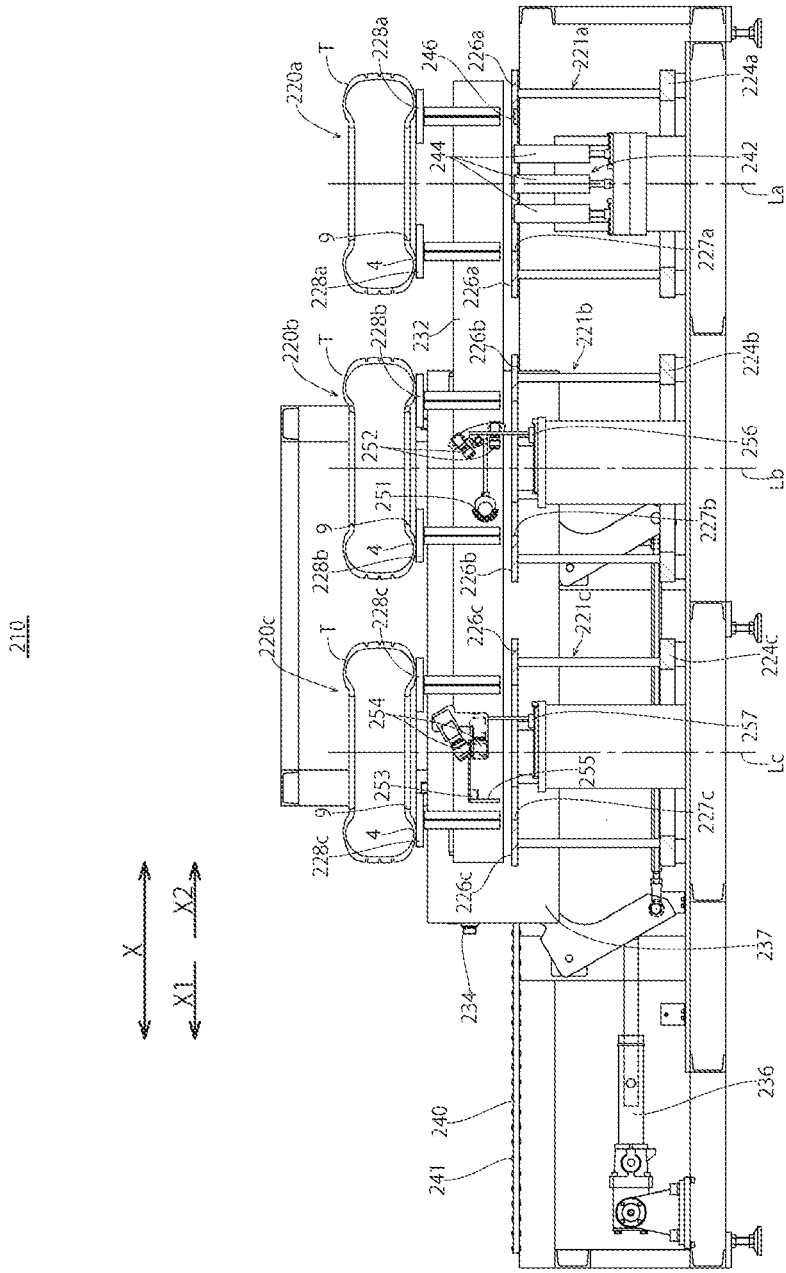
FIG. 19 is a diagram that shows a motion of the inspection device of the tire according to the third embodiment.

The transport mechanism 231 vertically moves the connection body 232 provided in the base plate 237 along the second linear guide 235 by the motion of the driving portion 236, and vertically moves the transport support portion 228*a*, the transport support portion 228*b*, and the transport support portion 228*c* fixed to the connection body 232 between a lower position of disposing the portions in the lower side than the support piece 226*a*, the support piece 226*b* and the support piece 226*c* shown in FIG. 14 and an upper position of disposing the portions in the upper side than the pieces shown in FIG. 19.

Furthermore, the transport mechanism 231 moves the connection body 232 along the first linear guide 233 by the motion of the first motor 234 by a gap of the inspection portions adjacent to each other in the arrangement direction X of the inspection portion back and forth. As a result, the transport mechanism 231 moves the transport support portion 228*a* from the first inspection portion 220*a* to the second inspection portion 220*b* adjacent thereto back and forth, moves the transport support portion 228*b* from the second inspection portion 220*b* to the third inspection portion 220*c* adjacent thereto back and forth, and moves the transport support portion 228*c* from the third inspection portion 220*c* to the carry-out table 240 adjacent thereto back and forth.

Moreover, in the first inspection portion 220*a*, as shown in FIGS. 14 and 15, a positioning mechanism 242 adjusting the position of the tire T, and a tire information acquisition portion 246 are provided.

The positioning mechanism 242 adjusts the position of the tire T such that the rotation axis Lt of the tire T of the inspection target placed from the outside of the inspection device 210 coincides with the rotation shaft La of the rotation table 221*a* of the first inspection portion 220*a*.

Specifically, the positioning mechanism 242 includes a plurality (for example, four in the present embodiment) of movers 244 in the inside of the cavity portion 227 of the rotation table 221*a*. The plurality of movers 244 is configured so as to be moved in the above and below direction, and synchronously moved in the directions of approaching the rotation axis La and being separated therefrom so that the movers are situated on the same circumference around the rotation axis La of the rotation table 221*a*. When the tire T is placed on the rotation table 221*a* of the first inspection portion 220*a* so that the hollow portion 9 of the tire T is vertically connected to the cavity portion 227 of the rotation table 221*a*, such a positioning mechanism 242 inserts a plurality of movers 244 into the hollow portion 9 of the tire T from the lower portion, and then, synchronously moves the plurality of movers 244 in the direction of being separated from the rotation axis La of the rotation table 221*a*. As a result, the plurality of movers 244 comes into contact with the bead portion 2 of the tire T placed on the rotation table 221*a*, whereby the position of the tire T is adjusted so that the rotation axis Lt of the tire T coincides with the rotation axis La of the rotation table 221*a* of the first inspection portion 220*a*.

The tire information acquisition portion 246 includes, for example, a barcode reader that reads a barcode label attached to the side wall portion 4 of the tire T. On the barcode label, for example, tire information including the kind of the tire T is shown, and the tire information acquisition portion 246 acquires the tire information shown on the barcode label.

In the second inspection portion 220*b* and the third inspection portion 220*c*, the inspection of the tire T is performed while rotating the tire T supported by the rotation table 221*b* and the rotation table 221*c*. In addition, the inspection performed in the second inspection portion 220*b* and the third inspection portion 220*c* is not particularly limited, but, as an example, the inner peripheral surface of the tire T is photographed by a camera and it is inspected whether or not the defect exists in the tire.

In the second inspection portion 220*b*, an illumination device 251, which illuminates the inner peripheral surface of the tire T placed on the rotation table 221*b* of the second inspection portion 220*b*, and a camera 252, which photographs the inner peripheral surface of the tire T, are disposed inside the cavity portion 227b of the rotation table 221b. The illumination device 251 and the camera 252 are connected to an inspection driving mechanism 256 and are provided so that they can come close to and be separated from the inner peripheral surface of the tire T placed on the rotation table 221b. In the second inspection portion 220b, the illumination device 251 is disposed along the inner peripheral surface of the tire T, and the camera 252 photographs the inner peripheral surface of the tire T in the state of irradiating light toward the circumferential direction of the tire T.

In the third inspection portion 220c, an illumination device 253, which illuminates the inner peripheral surface of the tire T placed on the rotation table 221c of the third inspection portion 220c, a camera 254, which photographs the inner peripheral surface of the tire T, and a mirror 255, which is curved along the circumferential direction of the inner peripheral surface of the tire T and reflects the light lighting the inner peripheral surface of the tire T to the camera 254, are disposed inside the cavity portion 227c of the rotation table 221c. The illumination device 253, the camera 254, and the mirror 255 are connected to the inspection driving mechanism 257 and are provided so that they can come close to and be separated from the inner peripheral surface of the tire T placed on the rotation table 221c. In the third inspection portion 220c, in the state in which the illumination device 253 illuminates the inner peripheral surface of the tire T, the camera 254 photographs the inner surface from the side wall portion 4 projected on the mirror 255 disposed along the inner peripheral surface of the tread portion 1 of the tire T to the bead portion 2.

The carry-out table 240 is a roller conveyor which is equipped with a plurality of rollers 241 and on which the tire T transported from the third inspection portion 220c is placed, and carries out the tire T to the outside of the inspection device 210.

Next, the motion of the inspection device 210 of the above configuration will be described with reference to FIGS. 16 to 22.

Figure 16:
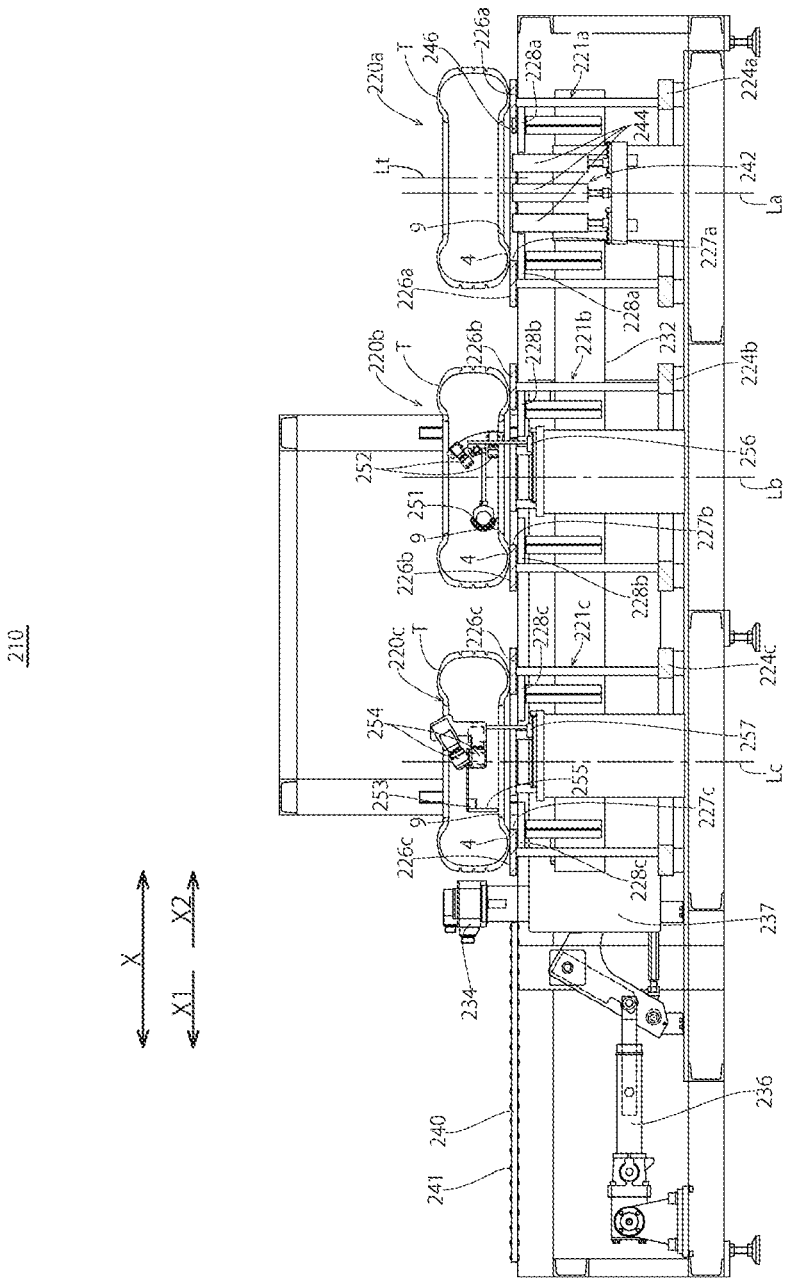
FIG. 16 is a diagram that shows a motion of the inspection device of the tire according to the third embodiment.

Firstly, as shown in FIG. 16, the tire T is placed on the rotation table 221a of the first inspection portion 220a from the outside of the inspection device 210 in the state of disposing the transport support portions 228a, 228b, and 228c in the lower position. In addition, a case will be described herein where the tire T is placed on the rotation table 221b of the second inspection portion 220b and the rotation table 221c of the third inspection portion 220c in advance.

Figure 17:
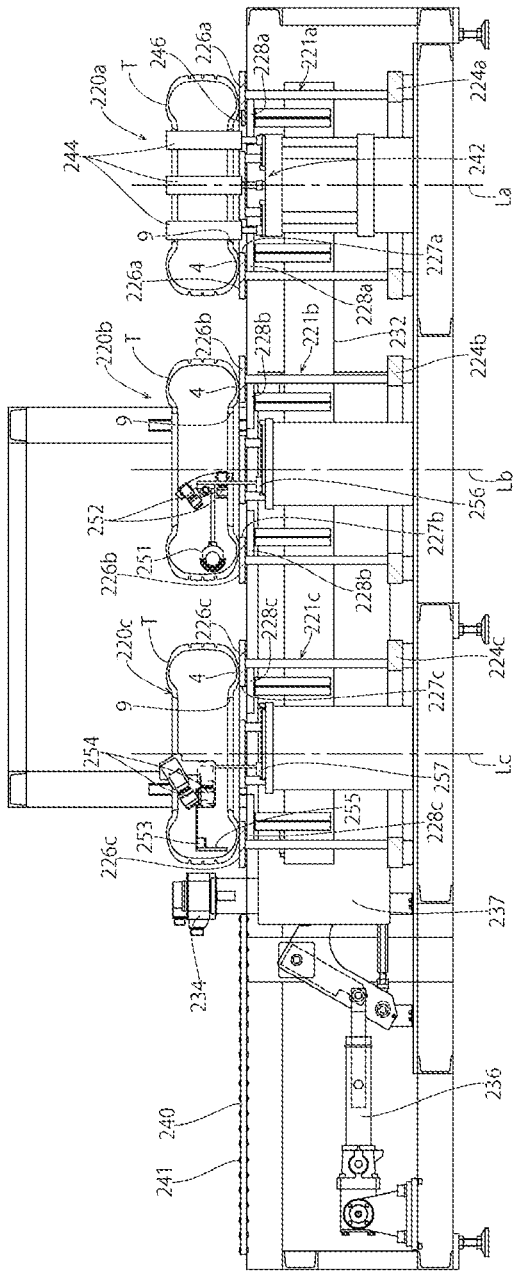
FIG. 17 is a diagram that shows a motion of the inspection device of the tire according to the third embodiment.

Next, as shown in FIG. 17, when the tire T is placed on the rotation table 221a of the first inspection portion 220a, the positioning mechanism 242 adjusts the position of the tire T such that the rotation axis Lt of the tire T coincides with the rotation axis La of the rotation table 221a of the first inspection portion 220a.

Figure 18:
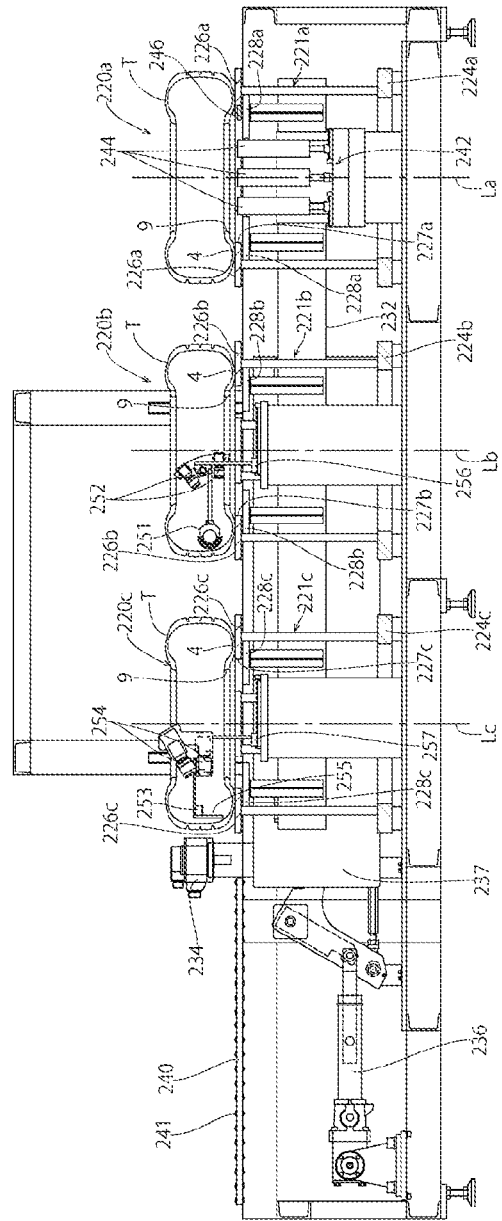
FIG. 18 is a diagram that shows a motion of the inspection device of the tire according to the third embodiment.

When the position adjustment of the tire T is completed, as shown in FIG. 18, the tire information acquisition portion 246 reads the barcode label attached to the side wall portion 4 of the tire T to acquire the tire information of the tire T, while driving the rotation driving portion 224a to rotate the tire T placed on the rotation table 221a around the rotation axis L thereof. When the position adjustment of the tire T and the acquisition of the tire information are performed in the first inspection portion 220a, in the second inspection portion 220b and the third inspection portion 220c, the inner peripheral surface of the tire T is photographed by the camera 252 and the camera 254 to perform the inspection of the tire T, while rotating the tire T supported by the rotation table 221b and the rotation table 221c.

Next, as shown in FIGS. 14 and 19, the transport mechanism 231 moves the connection body 232 upward along the second linear guide 235 of the connection body 232 and moves the transport support portions 228a, 228b, and 228c disposed in the lower position to the upper position. As a result, the tire T placed on the rotation table 221a of the first inspection portion 220a is transferred to the transport support portion 228a and is lifted to the upside of the rotation table 221a. Furthermore, the tire T placed on the rotation table 221b of the second inspection portion 220b or the rotation table 221c of the third inspection portion 220c is transferred to the transport support portion 228b and the transport support portion 228c and is lifted to the upside of the rotation table 221b and the rotation table 221c.

Figure 20:
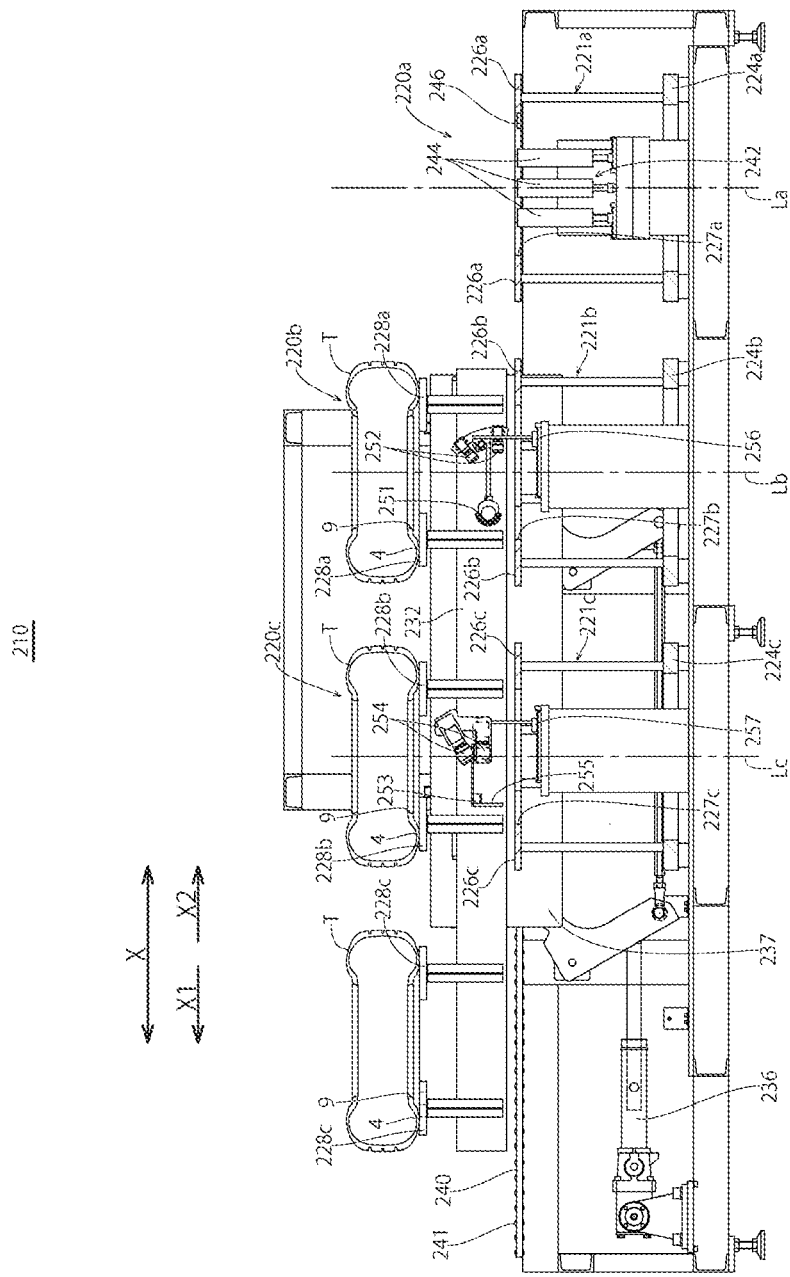
FIG. 20 is a diagram that shows a motion of the inspection device of the tire according to the third embodiment.

Next, as shown in FIGS. 19 and 20, the transport mechanism 231 moves the connection body 232 to one direction X1 of the arrangement direction X (hereinafter, the direction is called the arrangement direction) of the inspection portion along the first linear guide 233 so that the transport support portion 228a of the first inspection portion 220a is situated to the upside of the second inspection portion 220b, and disposes the tire T to the upside of the second inspection portion 220b. Along with the movement if the connection body 232 to the arrangement direction front X1, the transport support portion 228b is moved to the upside of the third inspection portion 220c to dispose the tire T upside the third inspection portion 220c, and the transport support portion 228c is moved to the upside of the carry-out table 240 and disposes the tire T upside the carry-out table 240.

Figure 21:
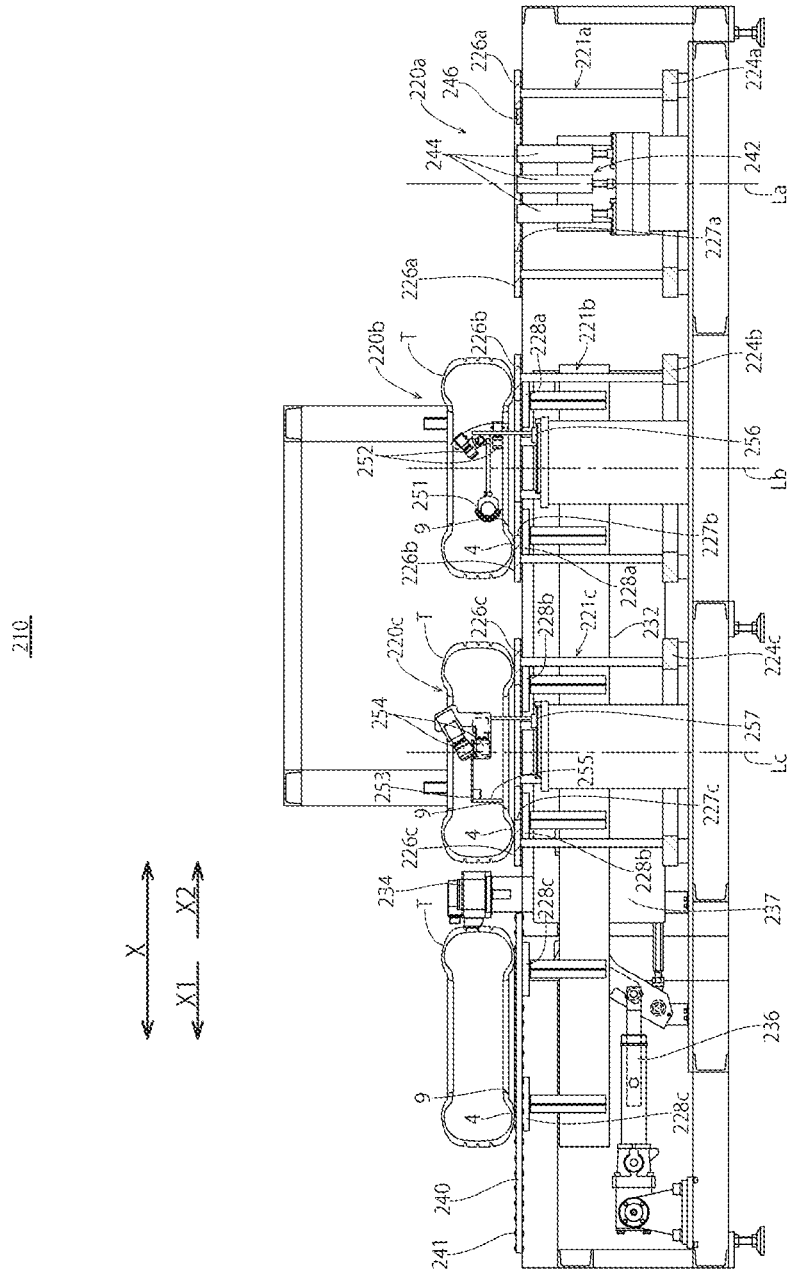
FIG. 21 is a diagram that shows a motion of the inspection device of the tire according to the third embodiment.

Next, as shown in FIGS. 14 and 21, the transport mechanism 231 moves the connection body 232 to the lower side along the second linear guide 235, moves the transport support portions 228a, 228b, and 228c situated in the upper position to the lower position, transfers the tire T disposed to the upside of the second inspection portion 220b from the transport support portion 228a to the support piece 226b of the second inspection portion 220b, transfers the tire T disposed to the upside of the third inspection portion 220c from the transport support portion 228b to the support piece 226c of the third inspection portion 220c, and transfers the tire T disposed to the upside of the carry-out table 240 from the transport support portion 228c to the roller 241 of the carry-out table 240.

As a result, the tire T in which the position adjustment of the tire T and the acquisition of the tire information are completed in the first inspection portion 220a, is moved from the rotation table 221a of the first inspection portion 220a to the rotation table 221b of the second inspection portion 220b, the tire T in which the inspection is completed in the second inspection portion 220b, is moved from the rotation table 221b of the second inspection portion 220b to the rotation table 221c of the third inspection portion 220c, and the tire T in which the inspection is completed in the third inspection portion 220c, is placed from the rotation table 221c of the third inspection portion 220c onto the roller 241 of the carry-out table 240. That is, in the present embodiment, the tire T is moved on the respective inspection portions 220a, 220b, and 220c to the arrangement direction front X1 of the inspection portion, whereby the first inspection portion 220a becomes an inspection portion situated in the most upstream side of the tire in the movement direction.

In addition, until the tire T is moved from the rotation table 221a to the rotation table 221b, the kind of the tire T is distinguished from the tire information acquired by the tire information acquisition portion 246, and the disposition of the illumination device 251 and the camera 252 provided in the second inspection portion 220b is set under the condition to be determined from the kind of the distinguished tire T. That is, the disposition of the illumination device 251 and the camera 252 provided in the second inspection portion 220b is set as the inspection condition in advance for each kind of the tire T, and the illumination device 251 and the camera 252 are moved so as to meet the inspection condition depending on the kind of the distinguished tire T in the first inspection portion 220a.

Furthermore, even in regard to the disposition of the illumination device 253, the camera 254 and the mirror 255 provided in the third inspection portion 220c, such a disposition is set as the inspection condition in advance for each kind of the tire T, and the illumination device 253, the camera 254, and the mirror 255 are moved so as to meet the inspection condition depending on the kind of the distinguished tire T in the first inspection portion 220a.

Figure 22:
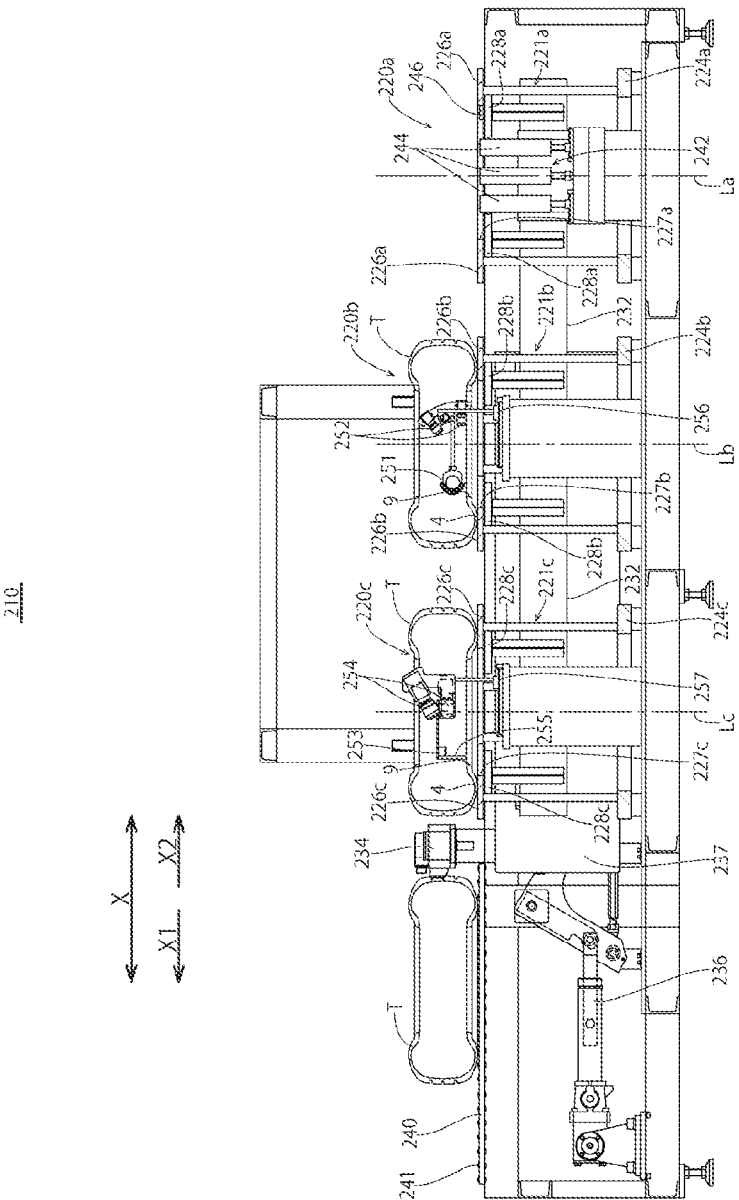
FIG. 22 is a diagram that shows a motion of the inspection device of the tire according to the third embodiment.

Next, as shown in FIGS. 14 and 22, the transport mechanism 231 moves the connection body 232 along the first linear guide 233 in an opposite direction (hereinafter, the direction is called an arrangement direction rear) X2 of the arrangement direction front X1, and restores the transport support portions 228a, 228b, and 228c to the positions of the first inspection portion 220a, the second inspection portion 220b, and the third inspection portion 220c, respectively.

At this time, the transport support portions 228a, 228b, and 228c are moved on the lower portions of the support pieces 226a, 226b, and 226c toward the arrangement direction rear X2, but, in some cases, the fulcrums 230a, 230b, and 230c provided on the lower surfaces of the support pieces 226a, 226b, and 226c disturb the movement of the transport support portions 228a, 228b, and 228c to the arrangement direction rear X2.

Figure 23:
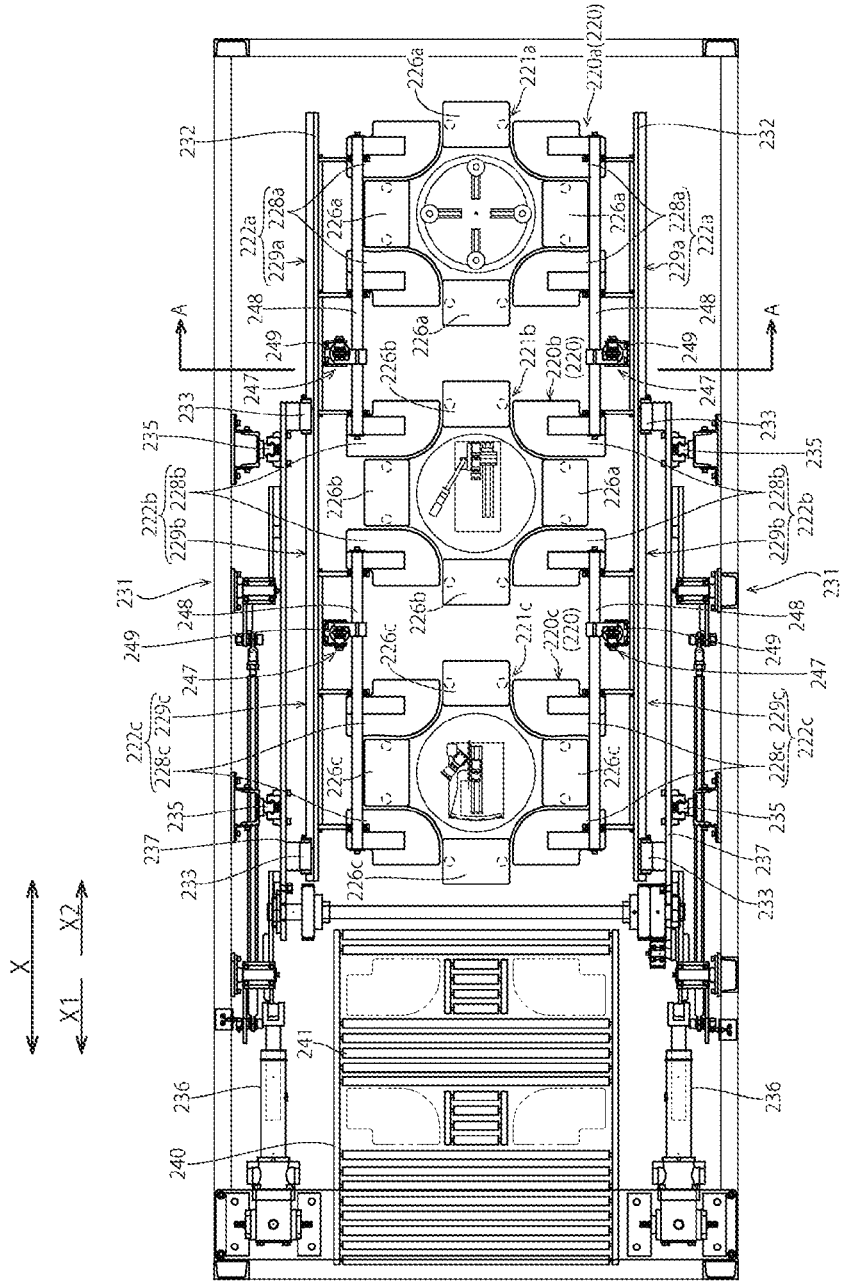
FIG. 23 is a plan view of an inspection device of a tire according to a modified example of the third embodiment.
Figure 24A:
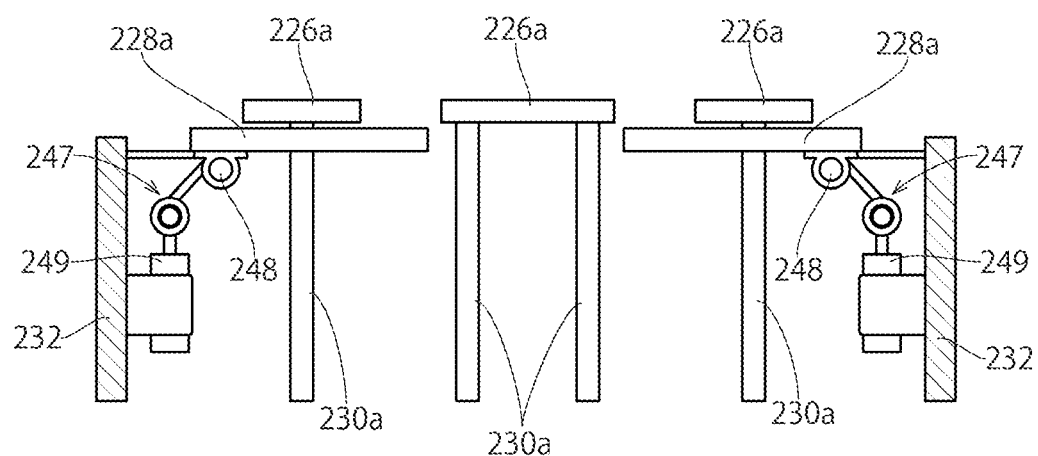
FIG. 24A is a cross-sectional view taken along the line A-A of FIG. 23 showing a state before a transport support portion is moved in a direction of being separated from a rotation axis of a rotation table.
Figure 24B:
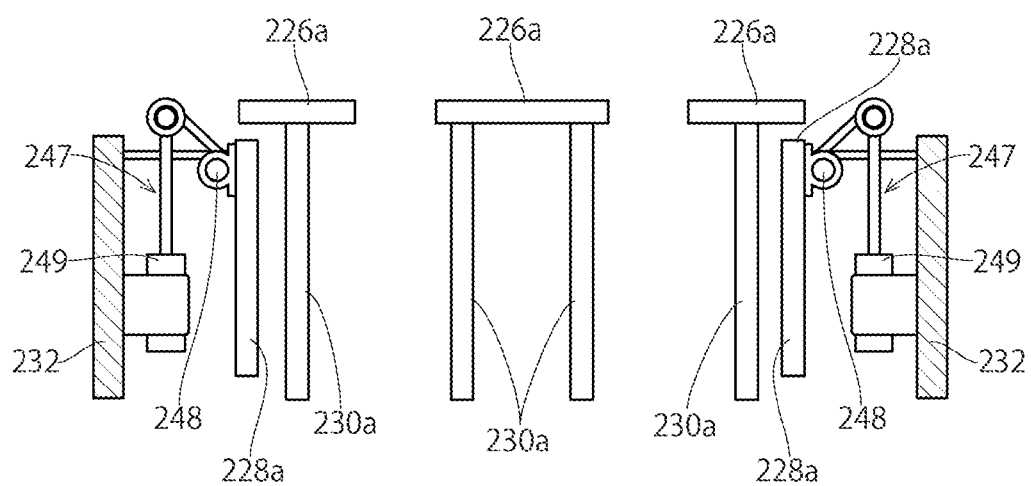
FIG. 24B is a cross-sectional view taken along the line A-A of FIG. 23 showing a state after a transport support portion is moved in a direction of being separated from a rotation axis of a rotation table.

In such a case, as shown in FIGS. 23, 24a, and 24b, a movement mechanism 247 may be provided which moves the transport support portions 228a, 228b, and 228c in a direction of being separated from the rotation axes La, Lb, and Lc of the rotation tables 221a, 221b, and 221c. Specifically, the movement mechanism 247 includes a rotation shaft 248 mounted on end portions of the connection body 232 side of the transport support portions 228a, 228b, and 228c, and a rotation driving portion 249 that rotates the rotation shaft 248. The rotation driving portion 249 rotates the rotation shaft 248 so that the tips of the transport support portions 228a, 228b, and 228c are directed to the lower side from the state in which the transport support portions 228a, 228b, and 228c as shown in FIG. 24A are protruded horizontally from the connection body 232, whereby the movement mechanism 247 moves the transport support portions 228a, 228b, and 228c in the direction of being separated from the rotation axes La, Lb, and Lc of the rotation tables 221a, 221b, and 221c.

Moreover, the tire T is placed on the rotation table 221a of the first inspection portion 220a from the outside of the inspection device 210 again (see FIG. 16), the position adjustment of the tire T and the acquisition of the tire information (see FIG. 17) in the first inspection portion 220a and the inspection of the tire T in the second inspection portion 220b and the third inspection portion 220c is performed (see FIG. 18), and then the movement of the transport support portions 228a, 228b, and 228c to the upper position (see FIG. 19), the movement of the transport support portions 228a, 228b, and 228c to the arrangement direction front X1 (see FIG. 20), the movement of the transport support portions 228a, 228b, and 228c to the lower position (see FIG. 21), and the movement of the transport support portions 228a, 228b, and 228c to the arrangement direction rear X2 (see FIG. 22) are sequentially and repeatedly performed, whereby the inspection of the tire T is performed in the second inspection portion 220b and the third inspection portion 220c, while sequentially moving the tire T placed on the rotation table 221a of the first inspection portion 220a from the first inspection portion 220a to the carry-out table 240.

As mentioned above, in the inspection device 210 of the present embodiment, since the support pieces 226a, 226b, and 226c supporting the tire T on the rotation table 221 and the transport support portions 228a, 228b, and 228c supporting the tire T on the transport portions 222a, 222b, and 222c support the different positions of the side wall portion 4 of the tire T, the tire T can be transferred between the transport support portions 228a, 228b, and 228c and the rotation support portions 223a, 223b, and 223c by the vertical movement of the transport support portions 228a, 228b, and 228c, whereby the time necessary for the transport of the tire can be reduced and the inspection time can be reduced.

In addition, in the present embodiment, a case was also described where the movement mechanism 247, which moves the transport support portions 228a, 228b, and 228c in a radial direction, is provided in the inspection device 210, but in the inspection device 210, there is no need to move the transport support portions 228a, 228b, and 228c in the direction (the radial direction of the tire T) of being separated from the rotation axes La, Lb, and Lc of the rotation tables 221a, 221b, and 221c in order to transfer the tire T to the rotation support portions 223a, 223b, and 223c. Thus, the transport support portion 228 may be moved in the radial direction between transferring the tire T from the transport support portion 228 to the rotation support portion 223 and starting the rotation of the rotation support portion 233, and even when the transport support portion 228 is moved in the direction of being separated from the rotation axes La, Lb, and Lc of the rotation table, the transport time of the tire T is not lengthened.

Furthermore, in the inspection device 210 of the present embodiment, since the transport support portions 228a, 228b, and 228c provided in the plurality of inspection portions 220a, 220b, and 220c are connected by the connection body 232, the transport support portions 228a, 228b, and 228c supporting the tire T for the transportation to the adjacent inspection portion can be moved by the common transport mechanism 231, whereby the inspection device 210 can be cheaply manufactured.

Furthermore, in the inspection device 210 of the present embodiment, the positioning mechanism 242, which adjusts the position of the tire T so that the rotation axis Lt of the tire T coincides with the rotation axis La of the rotation table 221a of the first inspection portion 220a, is provided in the first inspection portion 220a that is situated in the most upstream side of the movement direction of the tire among the plurality of inspection portions 220a, 220b, and 220c. For that reason, the transport mechanism 231 moves the connection body 232 along the arrangement direction X by a gap of the adjacent inspection portion, whereby it is possible to cause the rotation axis Lt of the tire T to conform to the rotation axis Lb of the second inspection portion 220b or the rotation axis Lc of the third inspection portion 220c, which can greatly reduce the inspection time of the tire.

Furthermore, in the inspection device 210 of the present embodiment, when the kind of the tire T placed on the first inspection portion 220a in the first inspection portion 220a situated in the most upstream side of the tire T in the movement direction is distinguished and the tire T is moved to the adjacent inspection portion, the disposition of the illumination device 251 and the camera 252 provided in the second inspection portion 220b or the disposition of the illumination device 253, the camera 254, and the mirror 255 provided in the third inspection portion 220c are moved so as to meet the condition that is determined from the kind of the distinguished tire T. For that reason, it is possible to inspect the different kinds of tires without lengthening the inspection time.

What is claimed is:

1. An illumination device, comprising:
a light source unit which illuminates an inner peripheral surface of a tire by light that is irradiated from the light source unit, the light source unit including a base portion that has a plane perpendicular to the circumferential direction of the tire, and a light emitting portion that emits light, and the light emitting portion is provided on the plane of the base portion,
wherein the tire and the light source unit are relatively rotated around an axis of the tire, in the state of irradiating the light from the light source unit disposed along the inner peripheral surface of the tire toward a circumferential direction of the tire,
wherein the light source unit emits light in blue.

2. An illumination device, comprising:
a light source unit which illuminates an inner peripheral surface of a tire by light that is irradiated from the light source unit,
wherein the tire and the light source unit are relatively rotated around an axis of the tire, in the state of irradiating the light from the light source unit disposed along the inner peripheral surface of the tire toward a circumferential direction of the tire,
wherein the light source unit includes a light emitting portion that emits light for illuminating the inner peripheral surface of the tire, and a ring-shaped base portion with the light emitting portion provided thereon, and
wherein the light emitting portion is provided in a plane perpendicular to a rotation direction of the light source unit in the base portion, and forms a circular arc shape that bulges toward the inner peripheral surface of the tire.

3. An inspection device of a tire, comprising:
an inspection portion that has an illumination portion which illuminates an inner peripheral surface of a tire by light irradiated from a light source unit and a photographing portion which photographs the inner peripheral surface of the tire, and a driving portion that relatively rotates the tire and the inspection portion around an axis of the tire,
wherein the light source unit includes a base portion that has a plane perpendicular to the circumferential direction of the tire, and a light emitting portion that emits light, and the light emitting portion is provided on the plane of the base portion,
wherein the photographing portion photographs the inner peripheral surface of the tire, while the driving portion relatively rotates the tire and the inspection portion around the axis of the tire, in the state of irradiating the light from the light source unit disposed along the inner peripheral surface of the tire toward the circumferential direction of the tire, and
wherein the illumination portion emits blue light.

4. An inspection device of a tire comprising:
an inspection portion which has an illumination portion that illuminates an inner peripheral surface of a tire, a photographing portion that photographs an inner peripheral surface of the tire, and a mirror that is curved along a circumferential direction of the inner peripheral surface of the tire and reflects light illuminating the inner peripheral surface of the tire to the photographing portion; and
a driving portion that relatively rotates the tire and the inspection portion around the axis of the tire,
wherein the photographing portion photographs light from the inner peripheral surface of the tire reflected by the mirror disposed along the inner peripheral surface of the tire, while the driving portion relatively rotates the tire and the inspection portion around the axis of the tire, in a state in which the illumination portion illuminates the inner peripheral surface of the tire, and
wherein the illumination portion emits blue light.

5. The inspection device according to claim 4,
wherein the mirror is disposed along an inner surface of a tread portion of the tire and reflects light, which illuminates an inner surface of a side wall portion to a bead portion of the tire, to the photographing portion.

6. The inspection device according to claim 5,
wherein the illumination portion is provided in the mirror to irradiate light toward the inner surface of the side wall portion of the tire.

7. An inspection device of a tire, comprising:
a rotation table that rotates a tire around a rotation axis of the tire and a transport portion that transports the tire, and inspects the tire supported on the rotation table while rotating the tire,
wherein the rotation table includes a rotation support portion that supports a side wall portion of the tire, and a rotation driving portion that rotates the rotation support portion around the rotation axis of the tire,
wherein the transport portion includes a transport support portion that supports a position which avoids the position supported by the rotation support portion in the side wall portion of the tire, and a vertical driving portion that vertically moves the transport support portion, and
wherein the vertical driving portion moves the transport support portion with the tire placed thereon from an upper side of the rotation support portion to a lower side thereof to transfer the tire placed on the transport support portion to the rotation support portion, and moves the transport support portion from the lower side of the rotation support portion with the tire placed thereon to the upper side thereof to transfer the tire placed on the rotation support portion to the transport support portion.

8. The inspection device according to claim 7
wherein the transport portion includes a movement mechanism that moves the transport support portion in a direction of being separated from the rotation axis of the rotation table.

9. The inspection device according to claim 7, further comprising:
a positioning mechanism that adjusts the position of the tire supported on the rotation support portion to cause the rotation axis of the tire to conform to the rotation axis of the rotation table.

10. The inspection device according to claim 7,
wherein a plurality of inspection portions including the rotation table and the transport portion is provided at intervals,
wherein the plurality of transport portions includes the transport support portion provided for each inspection portion, a connection body that connects the transport support portions provided for each inspection portion, and a transport mechanism that vertically moves the connection body and moves the connection body in an arrangement direction of the inspection portion, and wherein the plurality of transport portions moves the transport support portion with the tire placed thereon to the upper side of the rotation support portion of the adjacent inspection portion, and then, moves the transport support portion to the lower side of the rotation support portion, thereby transferring the tire onto the rotation table of the adjacent inspection portion.

11. The inspection device according to claim 10,
wherein the plurality of transport portions sequentially moves the tire supported on the rotation table in the arrangement direction of the inspection portion, and
wherein, in the inspection portion situated in the most upstream side of the movement direction of the tire, a positioning mechanism is provided which adjusts the position of the tire supported on the rotation support portion to cause the rotation axis of the tire to conform to the rotation axis of the rotation table.

12. The inspection device according to claim 10,
wherein the plurality of transport portions sequentially moves the tire supported on the rotation table in the arrangement direction of the inspection portion, and
wherein the inspection portion situated in the most upstream side of the movement direction of the tire acquires tire information of the tire supported on the rotation table, and sets an inspection condition of the inspection portion that is situated in a downstream side from the inspection portion situated in the most upstream side based on the acquired tire information.

\* \* \* \* \*